(12) United States Patent
Hanover et al.

(10) Patent No.: US 7,699,783 B2
(45) Date of Patent: Apr. 20, 2010

(54) METHOD FOR IMAGING AND TREATING A BREAST

(75) Inventors: Barry K. Hanover, Park City, UT (US); Steven A. Johnson, Salt Lake City, UT (US); David Robinson, Park City, UT (US); James Wiskin, Salt Lake City, UT (US); David Borup, Salt Lake City, UT (US)

(73) Assignee: Techniscan, Inc., Salt Lake City, UT (US)

( * ) Notice: Subject to any disclaimer, the term of this patent is extended or adjusted under 35 U.S.C. 154(b) by 1020 days.

(21) Appl. No.: 11/154,006

(22) Filed: Jun. 15, 2005

(65) Prior Publication Data

US 2006/0009696 A1    Jan. 12, 2006

Related U.S. Application Data

(63) Continuation-in-part of application No. 10/821,407, filed on Apr. 8, 2004.

(60) Provisional application No. 60/580,416, filed on Jun. 16, 2004.

(51) Int. Cl.
*A61B 8/00* (2006.01)

(52) U.S. Cl. ........................ 600/459; 600/437

(58) Field of Classification Search ................. 600/437, 600/459
See application file for complete search history.

(56) References Cited

U.S. PATENT DOCUMENTS

| | | | |
|---|---|---|---|
| 3,963,933 A | 6/1976 | Henkes, Jr. | |
| 4,105,018 A | 8/1978 | Greenleaf et al. | |
| 4,222,274 A | 9/1980 | Johnson | |
| 4,252,125 A | 2/1981 | Iinuma | |
| 4,282,880 A | 8/1981 | Gardineer et al. | |
| 4,298,009 A | 11/1981 | Mezrich et al. | |
| 4,317,369 A | 3/1982 | Johnson | |
| 4,341,222 A | 7/1982 | Gardineer et al. | |
| 4,485,819 A | 12/1984 | Igl | |
| 4,509,368 A | 4/1985 | Whiting et al. | |
| 4,662,222 A | 5/1987 | Johnson | |
| 4,727,550 A | 2/1988 | Chang et al. | |

(Continued)

OTHER PUBLICATIONS

B.L.N. Kennett and N.J. Kerry, "Seismic Waves in a Stratified Half Space," Geophys. J.R. astr. Soc. 57, pp. 557-583, 1979.

(Continued)

*Primary Examiner*—Long V Le
*Assistant Examiner*—Saurel J Selkin
(74) *Attorney, Agent, or Firm*—Thorpe North & Western LLP

(57) ABSTRACT

A method for imaging and treating a breast of a patient includes: disposing the breast into a bath of medium; physically securing the breast and maintaining the breast in a repeatable position and in a repeatable shape with respect to a chest wall of the patient; scanning the breast with ultrasound signals from transducer arrays to create a three-dimensional image of the breast and to locate a position of a tumor or a lesion in the breast with respect to the three-dimensional image; and further treating the tumor or the lesion of the breast while maintaining the position and the shape of the breast with respect to the chest wall of the patient as during scanning.

37 Claims, 12 Drawing Sheets

U.S. PATENT DOCUMENTS

| | | | |
|---|---|---|---|
| 4,798,209 | A | 1/1989 | Klingenback et al. |
| 5,227,797 | A | 7/1993 | Murphy |
| 5,339,815 | A | 8/1994 | Liu et al. |
| 5,474,072 | A | 12/1995 | Shmulewitz |
| 5,490,840 | A * | 2/1996 | Uzgiris et al. .................. 604/22 |
| RE35,330 | E * | 9/1996 | Malone et al. .................. 606/28 |
| 5,588,032 | A | 12/1996 | Johnson et al. |
| 5,667,893 | A | 9/1997 | De Hoop et al. |
| 5,673,697 | A | 10/1997 | Thomas |
| 5,806,521 | A | 9/1998 | Morimoto et al. |
| 5,833,633 | A | 11/1998 | Sarvazyan |
| 5,985,850 | A * | 11/1999 | Falk et al. ...................... 514/54 |
| 5,999,836 | A | 12/1999 | Nelson et al. |
| 6,005,916 | A | 12/1999 | Johnson et al. |
| 6,019,724 | A | 2/2000 | Gronningsaeter et al. |
| 6,027,447 | A | 2/2000 | Li |
| 6,056,700 | A * | 5/2000 | Burney et al. ................ 600/564 |
| 6,304,770 | B1 | 10/2001 | Lee et al. |
| 6,409,668 | B1 | 6/2002 | Wollschlaeger |
| 6,480,565 | B1 | 11/2002 | Ning |
| 6,494,844 | B1 * | 12/2002 | Van Bladel et al. ......... 600/567 |
| 6,544,186 | B1 | 4/2003 | Shelby et al. |
| 6,546,279 | B1 * | 4/2003 | Bova et al. .................. 600/429 |
| 6,587,540 | B1 | 7/2003 | Johnson et al. |
| 6,636,584 | B2 | 10/2003 | Johnson et al. |
| 6,782,759 | B2 | 8/2004 | Shank et al. |
| 6,860,855 | B2 | 3/2005 | Shelby et al. |
| 7,094,205 | B2 | 8/2006 | Marmarelis |
| 7,264,592 | B2 | 9/2007 | Shehada |
| 7,285,092 | B2 | 10/2007 | Duric et al. |
| 2002/0065461 | A1 | 5/2002 | Cosman |
| 2002/0131551 | A1 | 9/2002 | Johnson et al. |
| 2003/0097066 | A1* | 5/2003 | Shelby et al. ................ 600/443 |
| 2004/0064046 | A1 | 4/2004 | Shehada |
| 2004/0082856 | A1 | 4/2004 | Marmarelis |
| 2006/0173304 | A1* | 8/2006 | Wang ........................... 600/437 |

OTHER PUBLICATIONS

Brent S. Robinson and James F. Greenleaf, "An Experimental Study of Diffraction Tomography Under the Born Approximation," Acoustical Imaging 18, No. 18, Jun. 1990.

Cohen, J.K. and F.G. Hagin. "Velocity lnverison using a Stratifeid Refernece." *Geophysics*. 50, 11, 1985.

E. Crase, A. Pica, M. Noble, J. McDonald, and A. Tarantola, "Robust Elastic Nonlinear Waveform Inversion: Application to Real Data," Geophysics, 55, 5 (May 1990).

E.J. Ayme-Bellegarda and T.M. Habashy, "Forward Ultrasonic Scattering from Multidimensional Solid or Fluids Inclusions Buried in Multilayered Elastic Structures," IEEE Trans. Ultras., Ferro., and Freq. Cont., vol. 39, No. 1, Jan. 1992.

E.J. Ayme-Bellegarda, and T.M. Habashy, "Ultrasonic Inverse Scattering of Multidimensional Objects Buried in Multilayered Elastic Background Structures," IEEE Trans. Ultras., Ferro, and Freq. Cont., vol. 39, No. 1, Jan. 1992.

G.R. Franssens, "Calculation of the Elasto-dynamic Green's Function in Layered Media by Means of a Modified Propagator Matrix Method," Geophys. J.R. astr. Soc. 1983.

G.S. Pan, R.A Phinney and R.I. Odom, "Full-waveform Inversion of Plane-wave Seismograms in Stratified Acoustic Media: Theory and Feasibility," Geophysics, vol. 53, 1 (1988).

Kostas T. Ladas and A. J. Devaney, "Iterative Methods in Geophysical Diffraction Tomography," Inverse Problems 8 (1992).

M.J. Berggren, S.A. Johnson, B.L. Carruth, W.W. Kim, F. Stenger and P.L. Kuhn, "Performance of Fast Inverse Scattering Solutions for the Exact Helmholtz Equation Using Multiple Frequencies and Limited Views," Acoustical Imaging 15, Halifax, Nova Scotia, Jul. 1986.

M.J. Berggren, S.A. Johnson, W.W. Kim, D.T. Borup, R.S. Eidens and Y. Zhou, "Acoustic Inverse Scattering Images from Simulated Higher Contrast Objects and from Laboratory Test Objects," Acoustical Imaging 16, Chicago, Illinois, Jun. 1987.

P.R. Williamson, "Tomographic inversion in reflection seismology," Geophys. J. Int. 100, pp. 255-274, 1990.

Peter Mora, "Nonlinear Two-dimensional Elastic Inversion of Multi offset Seismic Data," Geophysics, vol. 52, Sep. 9, 1987.

R.J. Wombel and M.A. Fiddy (1988), "Inverse Scattering Within the Distorted-wave Born Approximation," Inverse Problems 4 (1988).

S.J. Norton, "iterative Seismic Inversion," Gerphusical Journal, No. 94, pp. 457-468 (1988).

T.K. Sarkar, E. Arkas, and S.M. Rao (1986) "Application of FFT and the Conjugate Gradient Method for the Solution of Electromagnetic Radiation from Electrically Large and Small Conducting Bodies," IEEE Trans. Antennas Propagat., vol. AP-34, pp. 635-640, May.

W.W. Kim, D.T. Borup, S.A. Johnson, M.J. Berggren, and Y. Ahou, "Accelerated Inverse Scattering Algorithms for Highter Contract Objects," in 1987 IEEE Ultrasonics Symposium, 903-906, (IEEE Cat. No. 87ch2492-7).

W.W. Kim, S.A. Johnson, M.J. Berggren, F. Stenger and C.H. Wilcox, "Analysis of Inverse Scattering Solutions from Single Frequency, Combined Transmission and Reflection Data for the Helmholtz and Riccati Exact Wave Equations," Acoustical Imaging 15, pp. 359-369, Plenum Press (1987).

Y. Zhou, S.A. Johnson, M.J. Berggren, B. Carruth, and W.W. Kim, "Constrained Reconstruction of Object Acoustic Parameters from Noisy Ultrasound Scattering Data," Proc. of the IEEE 1987 Ultrasonics Symposium pp. 897-901 (1987).

Hanover, et al., U.S. Appl. No. 11/153,923, filed Jun. 15, 2005.
Hanover, U.S. Appl. No. 12/152,631, filed May 14, 2008.
Hanover, U.S. Appl. No. 12/152,637, filed May 14, 2008.
Hanover, U.S. Appl. No. 10/821,407, filed Apr. 8, 2004.
Hanover, U.S. Appl. No. 11/223,910, filed Sep. 9, 2005.
Hanover, U.S. Appl. No. 11/222,541, filed Sep. 9, 2005.
Hanover, U.S. Appl. No. 11/223,084, filed Sep. 9, 2005.
Hanover, U.S. Appl. No. 11/436,989, filed May 17, 2006.
Hanover, U.S. Appl. No. 11/437,001, filed May 17, 2006.

* cited by examiner

METHOD FOR IMAGING AND TREATING A BREAST

PRIORITY CLAIM

Priority of U.S. Provisional Patent Application Ser. No. 60/580,416, filed Jun. 16, 2004, is claimed, and which is herein incorporated by reference. This application is a continuation-in-part of U.S. patent application Ser. No. 10/821,407, filed Apr. 8, 2004, which is herein incorporated by reference.

RELATED APPLICATION(S)

This application is related to U.S. patent application Ser. No. 11/153,923, filed Jun. 15, 2005, entitled "Apparatus for Imaging and Treating a Breast," which is herein incorporated by reference.

BACKGROUND

1. Field of the Invention

The present invention relates generally to a method for maintaining the position and the shape of a patient's breast during scanning and treatment, such as biopsy, therapy and/or surgery.

2. Related Art

Other than skin cancer, breast cancer is the most common cancer among women, and is the second leading cause of cancer death in women, after lung cancer. According to the American Cancer Society, about 215,990 women in the United States will be found to have invasive breast cancer in 2004, and about 40,110 women will die from the disease.

Approximately 44.5 million women in the United States are screened for breast cancer each year with 10% or 4.5 million referred for a second diagnostic test. The latest American Cancer Society Breast Cancer Statistics report indicates that 1 in 7 women will get breast cancer during her lifetime. The current standard of care has significant problems, generating unacceptably high rates of false positive tests—between 8% and 10%—and upwards of 15% false negative tests. The result is that many women suffer from unnecessary and invasive biopsies. In addition, each year the U.S. healthcare system spends an estimated $2.1 billion on biopsies, which yield negative results more than 75% of the time.

Breast cancer is a malignant tumor that has developed from cells of the breast. A malignant tumor is a group of cancer cells that may invade surrounding tissues or spread (metastasize) to distant areas of the body. The female breast is made up mainly of lobules (milk-producing glands), ducts (milk passages that connect the lobules to the nipple), and stroma (fatty tissue and connective tissue surrounding the ducts and lobules, blood vessels, and lymphatic vessels). Lymphatic vessels are like veins, except that they carry lymph instead of blood. Lymph is a clear fluid that contains tissue waste products and immune system cells (cells that are important in fighting infections). Lymph nodes are small bean-shaped collections of immune system cells that are found along lymphatic vessels. Cancer cells can enter lymphatic vessels and spread to lymph nodes. Most lymphatic vessels in the breast connect to lymph nodes under the arm (axillary lymph nodes). Some lymphatic vessels connect to lymph nodes inside the chest (internal mammary nodes) and either above or below the collarbone (supra- or infraclavicular nodes). When breast cancer cells reach the axillary (underarm) lymph nodes, they may continue to grow, often causing the lymph nodes in that area to swell. If breast cancer cells have spread to the underarm lymph nodes, they are more likely to have spread to other organs of the body as well. Thus, it is important to find out if breast cancer has spread to the axillary lymph nodes when choosing a treatment.

Most breast lumps are not cancerous, that is, they are benign. Most lumps turn out to be fibrocystic changes. The term "fibrocystic" refers to fibrosis and cysts. Fibrosis is the formation of fibrous (or scar-like) connective tissue, and cysts are fluid-filled sacs. Fibrocystic changes can cause breast swelling and pain. This often happens just before a period is about to begin. The breast may feel nodular, or lumpy, and, sometimes, a clear or slightly cloudy nipple discharge is noticed. Benign breast tumors such as fibroadenomas or papillomas are abnormal growths, but they are not cancer and cannot spread outside of the breast to other organs. They are not life threatening.

Although widespread use of screening mammography has increased the number of breast cancers found before they cause any symptoms, some breast cancers are not found by mammography, either because the test was not done or because even under ideal conditions mammography cannot find every breast cancer. The most common sign of breast cancer is a new lump or mass. A painless, hard mass that has irregular edges is more likely to be cancerous, but some rare cancers are tender, soft, and rounded. For this reason, it is important that a health care professional who is experienced in diagnosing breast diseases check any new breast mass or lump.

Other signs of breast cancer include a generalized swelling of part of a breast (even if no distinct lump is felt), skin irritation or dimpling, nipple pain or retraction (turning inward), redness or scaliness of the nipple or breast skin, or a discharge other than breast milk. Sometimes a breast cancer can spread to underarm lymph nodes even before the original tumor in the breast tissue is large enough to be felt.

If there is any reason to suspect breast cancer, other tests must be performed. After a complete physical exam (including a clinical breast exam), doctors often recommend a diagnostic mammogram or a breast ultrasound. A clinical breast examination (CBE) is an exam of the breasts by a health professional, such as a doctor, nurse practitioner, nurse, or physician assistant. The examiner first looks at the breasts for changes in size or shape. Then, using the pads of the finger tips, the breasts are felt for lumps.

Although mammograms are mostly used for screening, they can also be used to examine the breast of a woman who has a breast problem. This can be a breast mass, nipple discharge, or an abnormality that was found on a screening mammogram. In some cases, special images known as cone views with magnification are used to make a small area of altered breast tissue easier to evaluate. A diagnostic mammogram may show that a lesion (area of abnormal tissue) has a high likelihood of being benign (not cancer). In these cases, it is common to ask the woman to come back sooner than usual for a recheck, usually in 4 to 6 months. On the other hand, a diagnostic mammogram may show that the abnormality is not worrisome at all, and the woman can then return to having routine yearly mammograms. Finally, the diagnostic work-up may suggest that a biopsy is needed to tell if the lesion is cancer.

Ultrasound, also known as sonography, uses high-frequency sound waves to outline a part of the body. High-frequency sound waves are transmitted into the area of the body being studied and echoed back. A computer or dedicated electronic circuitry picks up the sound wave echoes and changes them into an image that is displayed on a computer screen. Breast ultrasound is sometimes used to evaluate breast abnormalities that are found during mammography or a physical exam. One of the most common abnormalities that women have is fibrocystic disease. Ultrasound is useful for detecting fibrocystic disease. It is the easiest way to tell if a cyst is present without placing a needle into it to draw out fluid. It can also find some breast masses. Conventional medical ultrasound uses a single ultrasound array to both transmit and receive echoes and thereby measure the ultrasound reflectivity and distance of various objects under the skin surface. It assumes that the speed of sound is constant through the tissue being imaged. It has difficulty imaging objects with low reflectivity or high absorption of sound. It produces images which are two-dimensional, distorted, grainy, and contain speckle. Foreground objects tend to mask deeper structures.

A biopsy is done when mammograms, ultrasound, or the physical examination finds a tumor. A biopsy is the only way to tell if cancer is really present. All biopsy procedures remove a tissue sample for examination under a microscope. There are several types of biopsies, such as fine needle aspiration biopsy, core (large needle) biopsy, and surgical biopsy. Each type of biopsy has distinct advantages and disadvantages. The choice of which to use will depend on the specific situation. Some of the factors the doctor will consider include how suspicious the lesion appears, how large it is, where in the breast it is located, how many lesions are present, other medical problems the patient may have, and the patient's personal preferences. Statistically, three of four biopsies are benign.

In addition, high rates of recall are currently being experienced in lumpectomy breast surgery. As many as 30-40% of excisional breast biopsies must be repeated due to post-surgical histological findings of malignant cells unacceptably close to the margin of excised breast tissue. The subsequent surgery is extremely costly as well as traumatic to the patient. Current methods in widespread use for guiding the surgeon to the outer margins of a malignant lesion are extremely crude and inaccurate. These methods generally involve the placement of one or more barbed wires under ultrasonic guidance or with no real-time guidance followed by post-placement positional checking with x-rays. Often the lesion cannot be clearly delineated from surrounding tissue and the wire(s) can be anywhere within or near the lesion. The relative position of the wire(s) is communicated verbally or in a report to the surgeon who must translate this information into removal of the malignant tissue while trying to preserve as much normal tissue as possible. The difference in the shape of the breast during wire placement and surgery can result in significant geometrical errors that substantially contribute to "dirty" margins and repeat surgeries.

One relatively new approach to improving surgery staging involves using contrast-enhanced MRI subtraction imaging to determine the location of malignant lesions in 3D. With the patient remaining in the MRI breast retention system, multiple MRI-safe wires are placed, with access to only the lateral side of each breast, at the outer poles of the lesion to guide the surgeon. The method has the benefit of more accurately defining the margins of the lesion and translating that information to the surgeon through the use of multiple wires that remain in position regardless of breast distortion. The downside to such a procedure is the cost of both the initial investment to purchase MRI equipment and, subsequently, the necessity of upgrading that MRI system to enable this procedure. In addition, the time required to image the patient and place the wires routinely exceeds one hour. Notwithstanding these potential barriers to use of MRI-guided wire placement, this procedure is gaining acceptance and local hospitals are budgeting to acquire the enabling MRI hardware and software upgrades at significant cost.

In order to facilitate diagnosis of breast cancer and reduce unnecessary biopsies, an improved and advanced tomography or ultrasonic scanning technology has been developed, referred to as Ultrasound CT™ by Techniscan Medical Systems of Salt Lake City, Utah. In addition, the Ultrasound CT™ system is intended to decrease the incidence of recall surgery due to inadequate margins. Ultrasound CT™ is ultrasound computerized tomography, and is intended to be used as an adjunct to mammography. The Ultrasound CT™ technology generates information using transmission ultrasound which produces two unique images: one of the speed of sound and one of the attenuation (absorption of sound at a sub millimeter resolution) throughout the breast. The underlying proposition is that these unique measurements will correlate to specific tissue properties. Radiologists then use the information to distinguish breast cancer from benign tumors or normal tissues.

Ultrasound CT™ produces a stack of tomography (2-D planar slice) images, similar in appearance and spatial resolution to CT or MR imaging methods, but at a much lower cost. These images are produced using two different techniques—Ultrasound Reflective Tomography (URT) and Ultrasound Inverse Scattering Tomography (UIST). Compared with conventional projection mammography Ultrasound CT™ images are more detailed, easier to read, and do not use potentially harmful ionizing radiation. Unlike conventional ultrasound, Ultrasound CT™ images completely penetrate and sample the entire breast for uniform and better overall resolution. These images are not dependent on the system operator for image quality and consistency. For example, see U.S. Pat. Nos. 4,662,222; 5,339,282; 5,588,032; 6,005,916; 6,587,540; and 6,636,584.

Once Ultrasound CT™ has been utilized to identify breast cancer, therapy and/or surgery can be utilized to neutralize or remove the tumor. However, a further biopsy may be required. Multiple testing or treatments, such as a mammogram, an Ultrasound CT™ scan, a possible biopsy, and therapy or surgery, can be stressful for the patient. In addition, the tumor or lesion needs to be relocated at each interval.

SUMMARY OF THE INVENTION

It has been recognized that it would be advantageous to develop a method to facilitate further treatment of the breast or tumor after performing a scan or creating a tomography of the breast. In addition, it has been recognized that it would be advantageous to develop a method to facilitate biopsy, therapy and/or surgery after an ultrasound computer topography scan. In addition, it has been recognized that it would be advantageous to develop a pre-biopsy, pre-therapy or pre-surgical staging method that uses inverse scattering ultrasound technology to accurately model in situ malignant breast legions in three-dimensions, and coordinates placement of a biopsy device, marker placement device, needle, probe, and/or surgical instrument.

The invention provides a method for imaging and treating a breast of a patient, including: disposing the breast into a bath of medium; physically securing the breast and maintaining the breast in a repeatable position and in a repeatable shape with respect to a chest wall of the patient; scanning the breast with ultrasound signals from transducer arrays to create a three-dimensional image of the breast and to locate a position of a tumor or a lesion in the breast with respect to the three-dimensional image; and further treating the tumor or the lesion of the breast while maintaining the position and the shape of the breast with respect to the chest wall of the patient as during scanning. Maintaining the position and the shape of the breast during further treatment allows for the tumor or lesion to be more easily located, and allows three-dimensional image to be utilized to guide treatment instruments.

In accordance with a more detailed aspect of the present invention, the patient can be positioned on a table with the breast pendent through an aperture in the table. In addition, the patient can be maintained on the table with the breast pendent through the aperture while further treating the tumor or the lesion. Maintaining the patient on the table can expedite treatment, maintains the known position of the tumor or lesion, and allows the three-dimension image to be utilized to guide treatment instruments.

In accordance with a more detailed aspect of the present invention, the breast can be secured to a frame suspended from a table supporting the patient.

In accordance with a more detailed aspect of the present invention, the further treatment can be performed with the breast in or out of the bath. If treatment is to be conducted out of the bath, then the breast can be removed the breast from the bath, and the position and the shape of the breast can be substantially maintained out of the bath as in the bath during scanning. A frame can be suspended from a table supporting the patient after the breast is removed from the bath, and the breast can be secured to the frame. Thus, the frame does not interfere with the bath or with scanning.

In accordance with a more detailed aspect of the present invention, physically securing the breast can include securing the breast to a structure within the bath.

In accordance with a more detailed aspect of the present invention, further treating the breast can include:

performing a biopsy by inserting a biopsy device into the tumor or lesion and removing a tissue sample;

inserting at least one marker into the breast using the biopsy device to mark a margin of the tumor to guide a surgeon during surgery to remove the tumor;

inserting at least one marker into the breast to mark a margin of the tumor to guide a surgeon during surgery to remove the tumor;

performing ultrasound ablation by directing ultrasound energy at the tumor;

injecting a chemotherapy drug into the tumor using a needle;

injecting an ultrasound activated drug into the patient, and directing ultrasound energy at the tumor;

thermally treating the tumor by inserting a probe with a hot tip or a cold tip into the tumor; and/or performing surgery to remove the tumor using a surgical instrument.

In accordance with a more detailed aspect of the present invention, the biopsy device, the marker placing device, the ultrasound emitter, the needle, the probe or the surgical instrument can be guided by a navigation system linked to the three-dimensional image. In addition, the navigation system can include:

a stereotactic frame secured to the breast, and the biopsy device, the marker placing device, the ultrasound emitter, the needle, the probe or the surgical instrument attached to the stereotactic frame;

a camera visually sensing an infrared marker on the biopsy device, the marker placing device, the ultrasound emitter, the needle, the probe or the surgical instrument; or a transmitter and receiver system coupled to the biopsy device, the marker placing device, the ultrasound emitter, the needle, the probe or the surgical instrument.

In accordance with a more detailed aspect of the present invention, performing ultrasound ablation can further include disposing the breast back into the bath of medium and substantially maintaining the position and the shape of the breast with respect to the chest wall of the patient as during scanning, prior to performing ultrasound ablation.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIGS. 4b and 4c are front views of a display of the navigation system of FIG. 4a;

FIG. 6b is a partial perspective view of the frame with the ultrasonic emitter of FIG. 6a;

FIG. 7b is a partial perspective view of the frame with the treatment instrument of FIG. 7a;

FIG. 8b is a partial perspective view of the scanning system of FIG. 8a;

FIG. 9b is a cross-sectional side view of the bath of FIG. 9a.

DETAILED DESCRIPTION OF EXAMPLE EMBODIMENT(S)

Figure 1A:
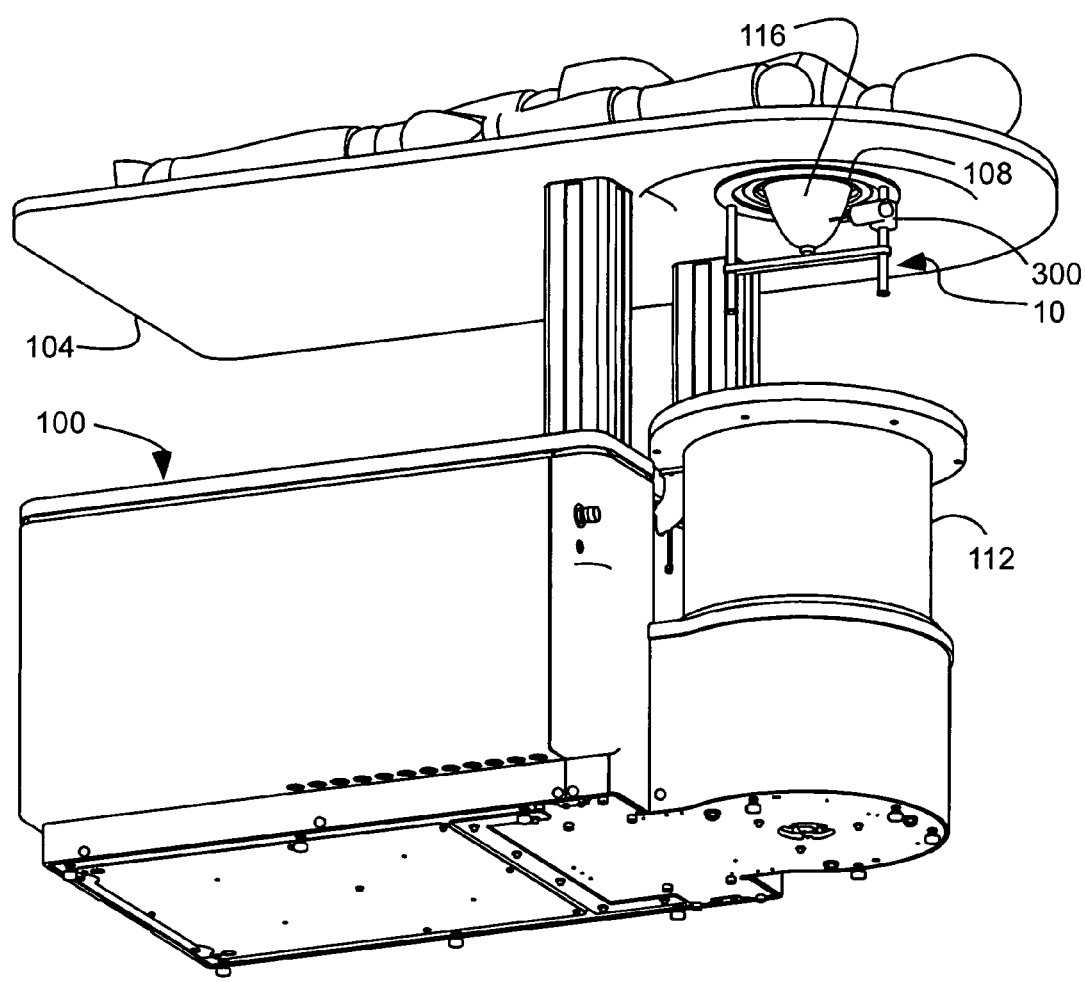
FIG. 1a is a perspective view of a frame for maintaining a position and a shape of a breast in accordance with an embodiment of the present invention disposed on a scanning system.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present invention includes a method for further treating a tumor or a lesion of a breast while maintaining a position and a shape of the breast with respect to the chest wall of the patient as during scanning. Maintaining the position and the shape of the breast during further treatment allows for the tumor or legion to be more easily located, and allows three-dimensional image to be utilized to guide treatment instruments. Scanning can include an ultrasound computerized tomography, such as Ultrasound Reflective Tomography (URT) and Ultrasound Inverse Scattering Tomography (UIST). The further treatment can include biopsy; marker placement; therapy and/or surgery. Therapy can include ultrasound ablation; injecting a drug into the tumor; injecting an ultrasound activated drug into the patient and directing ultrasound energy at the tumor to activate the ultrasound activated drug; and/or thermally treating the tumor by inserting a probe with a hot tip or a cold tip into the tumor. Furthermore, biopsy, therapy and/or surgery can be facilitated with a navigation system linked to a three-dimensional image or model of the breast generated from the scanning. The surgical navigation can utilize a sterotactic frame, a camera, or electro-magnetical signals to coordinate the position of a biopsy device, a marker placement device, a needle, a probe and/or a surgical instrument with respect to the three-dimensional image or model, and thus with respect to the breast and the tumor.

Referring to FIGS. 1a-2b, a breast retention mechanism or frame, indicated generally at 10, in accordance with the present invention is shown for maintaining the position and the shape of the breast as during scanning. The frame 10 can be part of a breast scanning and/or imaging system 100 shown for imaging or scanning a breast, as discussed in greater detail below. Generally, the system 100 includes a table 104 to receive a patient thereon and having an aperture 108 formed therein and disposable over bath 112 of medium so that the patient's breast 116 is pendent through the aperture and received in the bath. Transducer arrays 120 and 124 are disposed in the bath to transmit and receive ultrasound signals. The breast can be physically secured and maintained in a repeatable position and in a repeatable shape with respect to a chest wall of the patient, as described below.

Figure 1B:
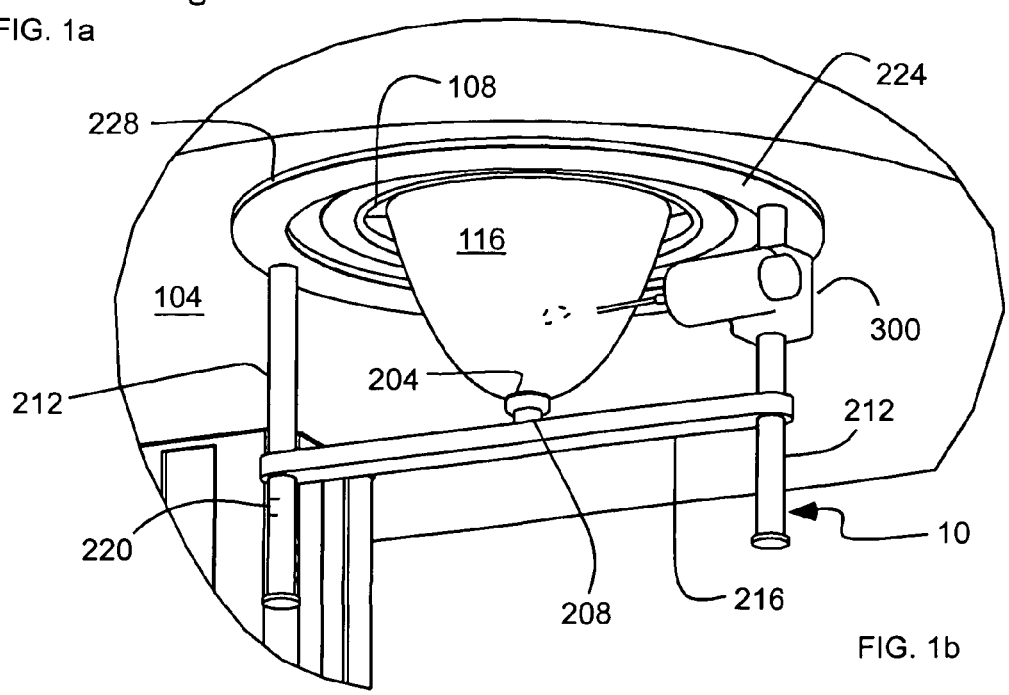
FIG. 1b is a partial perspective view of the frame of FIG. 1.
Figure 1C:
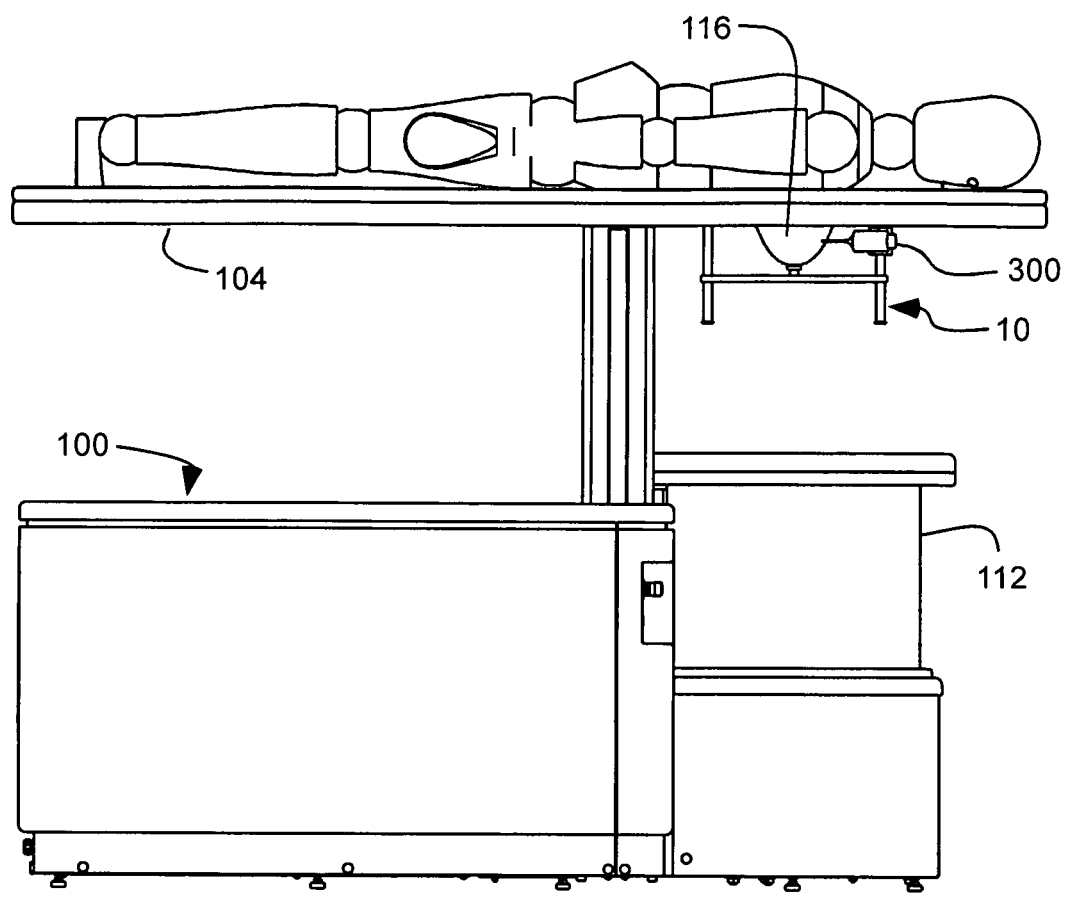
FIG. 1c is a side view of the frame and scanning system of FIG. 1.
Figure 3A:
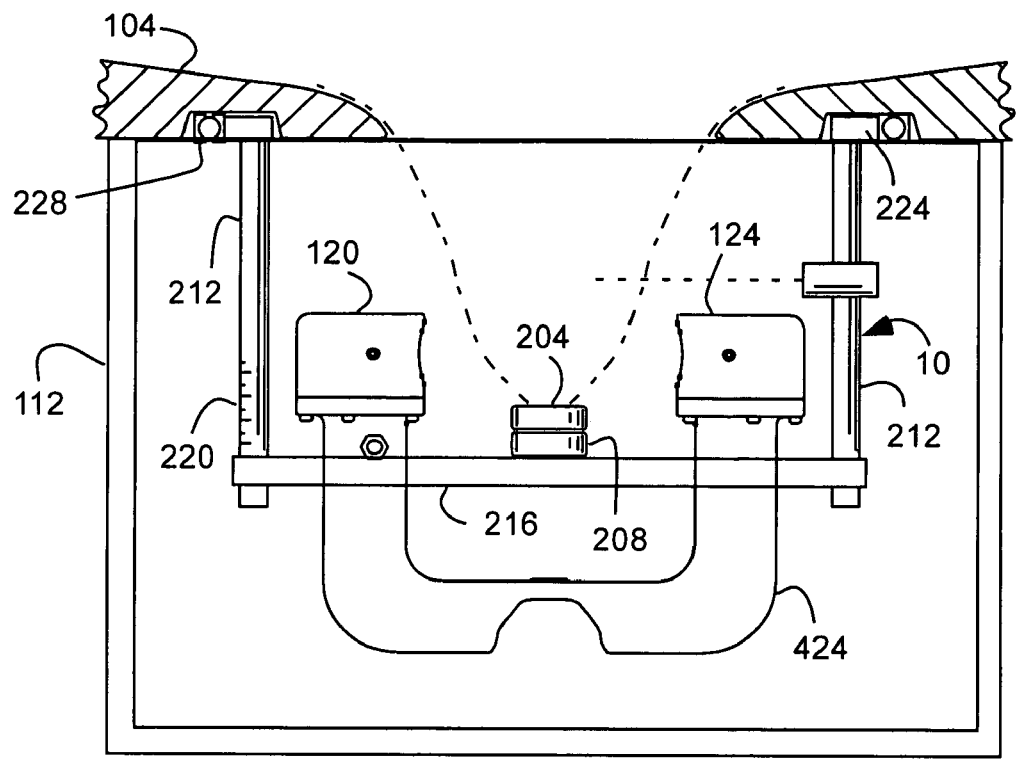
FIG. 3a is a side view of the frame of FIG. 1 shown disposed in a bath of the scanning system.
Figure 3B:
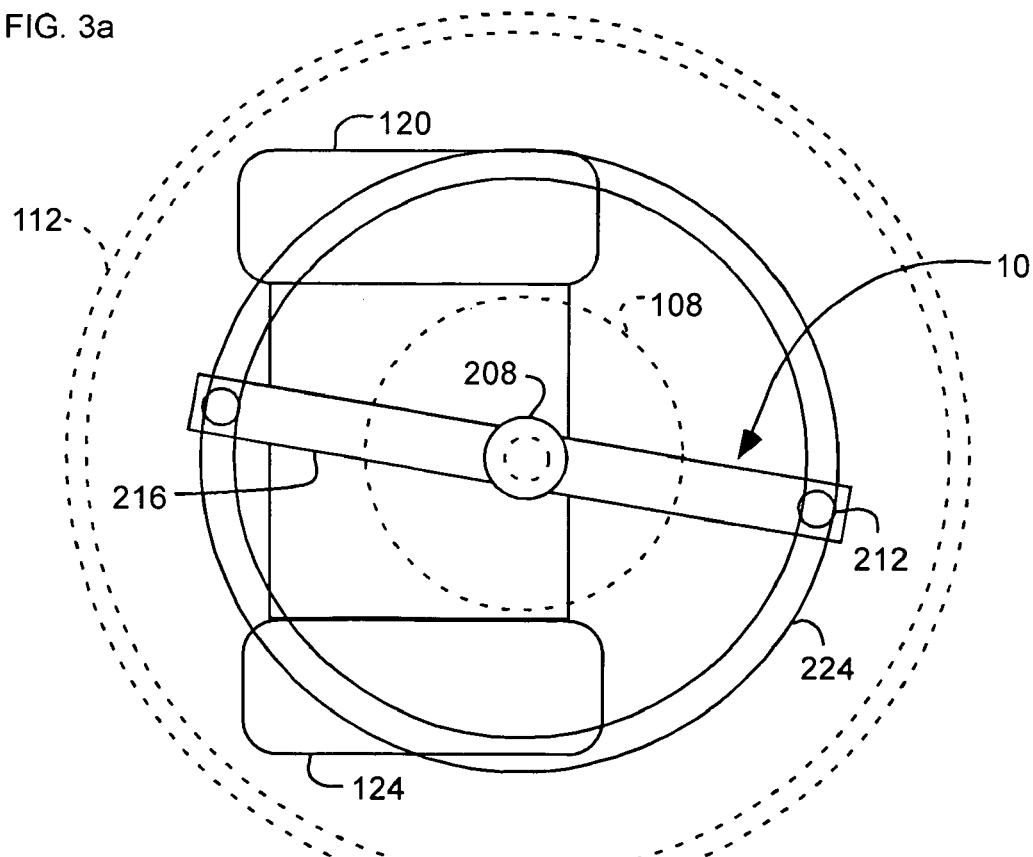
FIG. 3b is a top schematic view of the frame of FIG. 1.

The frame 10 can be disposed under the table 104 and carried by the table. The frame 10 can be removably attached to the table, such as with snap attachments or magnets or the like. Thus, the frame 10 can be secured to the table 104 when the table is elevated and the breast is removed from the bath, as shown in FIGS. 1a and 1c. The frame can be attached to the table and around the breast, and the breast can be secured to the frame. The frame can be configured to maintain the same position and the same shape of the breast as during scanning in the bath. Alternatively, the frame can be disposed in the bath and can maintain the position and the shape of the breast both in and out of the bath, as shown in FIGS. 3a and 3b.

A breast magnet 204 can be securable to the breast 116, such as at the nipple with an adhesive or the like. The frame can include a frame magnet 208 secured to the frame and engagable with the breast magnet 204. The breast and frame magnets 204 and 208 are an example of means for securing the breast to the frame. Other means for securing the breast to the frame could be used, including for example, snaps, a temporary adhesive, etc. While in the bath, the breast can be secured to a structure within the bath, such as with the breast magnet 204 engaging a bath magnet 210 secured on a rod.

As described below, the relative position of the breast or breast magnet 204 is determined while the breast is in the bath for scanning. The frame 10 can position the frame magnet 208 so that the frame and frame magnet maintain the breast in the same configuration as in the bath during scanning. Thus, the frame magnet 208 attached to the frame 10 can attach to the breast magnet 204 and position the nipple at the same relative position to the chest wall as during scanning.

The frame 10 mounted to the table 104 can permit the breast to remain in a known position for stereotaxic guided biopsy, surgery or therapy, as discussed below. The frame 10 can be mounted to the table 104, and the magnets 204 and 208 can immobilize the breast.

The frame 10 can include one or more posts 212 extending downwardly from the table, and a cross member 216 extending horizontally between the posts. The frame magnet 208 can be attached to the cross member 216. The cross member 216 can be movably coupled to the posts 212 to vertically position the frame magnet 208, and thus the breast magnet and breast. A scale 220 can be disposed on the posts 212 to facilitate proper positioning of the cross member, and thus the frame magnet. A ring 224 can be rotatably connected to the table, and can support and suspend the posts. The ring 224 can circumscribe the aperture 108 in the table. In addition, the ring 224 can be coupled to the table by a bearing 228 so that the ring and the frame can rotate in order to position the posts out of the way.

The frame 10 maintains the position and the shape of the breast after scanning, such as with the table raised and the breast elevated from the bath for treatment. Accurate placement of a treatment instrument, indicated by 300, can be achieved while the breast is constrained in the frame 10 attached to the underside of the elevated tabletop. Orientation of the frame can be mechanical- or laser-guided by computer-generated coordinates to provide the radiologist with the correct orientation and entry point for the treatment instrument. The depth for the treatment instrument can also be provided by computer and controlled mechanically or manually by the radiologist. Access to all sides of the breast is provided, unlike the lateral-only access provided with the MRI-based system. The position of treatment instrument could also be checked using scanning in order to verify the position. The treatment instrument 300 is shown generically in the figures and represents a biopsy device, a marker placement device, a needle, a probe or a surgical instrument.

In an alternative embodiment, as shown in FIGS. 3a and 3b, the breast retention mechanism or frame can be used for maintaining the position and the shape of the breast during both scanning in the bath, and during treatment. Thus, the patient's breast can be held or immobilized by securing the nipple or breast magnet 204 to the patient's nipple or breast, inserting the breast through the aperture 108 in the table 104, and magnetically coupling the nipple or breast magnet 204 to the frame magnet 208 of the frame 10. The patient's breast can be immobilized prior to insertion into the bath, and with the table elevated. Another bearing can be inserted between the magnets, or between the frame magnet and the frame. The bearing 228 can allow the frame 10, or posts 212 and cross-member 216, to rotate about the breast, thus rotating out of interference with the arrays during operation, and without twisting the patient's breast. The frame 10 can be pivoted when abutted by the arrays. Alternatively, magnets can be disposed between the frame and arrays to resist interference between the two.

Alternatively, the breast retention mechanism or the frame can be an extension of a rod movably disposed in the bath, and capable of being elevated out of the bath. Alternatively, the frame can be disposed on the rod.

Figure 4B:
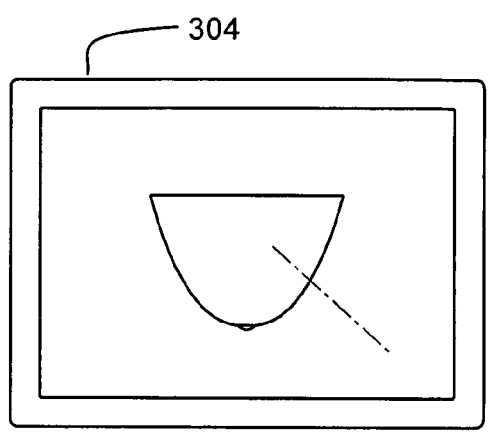
Figure 4C:
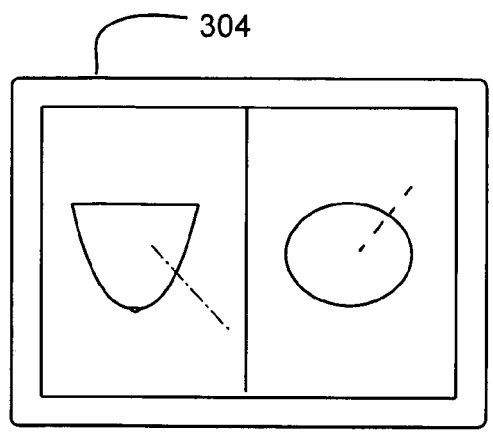

Maintaining the position and the shape of the breast during further treatment allows for the tumor or lesion to be more easily located, and allows three-dimensional image to be utilized to guide treatment instruments. The system 100 can include a navigation system linked to a three-dimensional image or model of the breast. Thus, the navigation system can aid in directing the treatment instrument 300 for biopsy, marker placement, therapy and/or surgery. The navigation system can track or sense the location and orientation of the treatment instrument 300 with respect to the three-dimensional image or model of the breast. In addition, the navigation system can display the location and orientation of the treatment instrument along with the three-dimensional image or model (and the tumor), such as on a monitor 304 (FIGS. 4*b* and 4*c*). Such a display can be three-dimensional (FIG. 4*b*), or can include two or more two-dimensional images (FIG. 4*c*).

The navigation system can use a mechanical reference, such as the frame 10 as a stereotactic frame. Thus, the treatment instrument 300 can be attached or coupled to the frame 10, as shown in FIGS. 1*a-d*. Thus, the position of the treatment instrument 300 with respect to the breast and tumor is known because the position of the frame with respect to the breast and tumor is known.

Figure 4A:
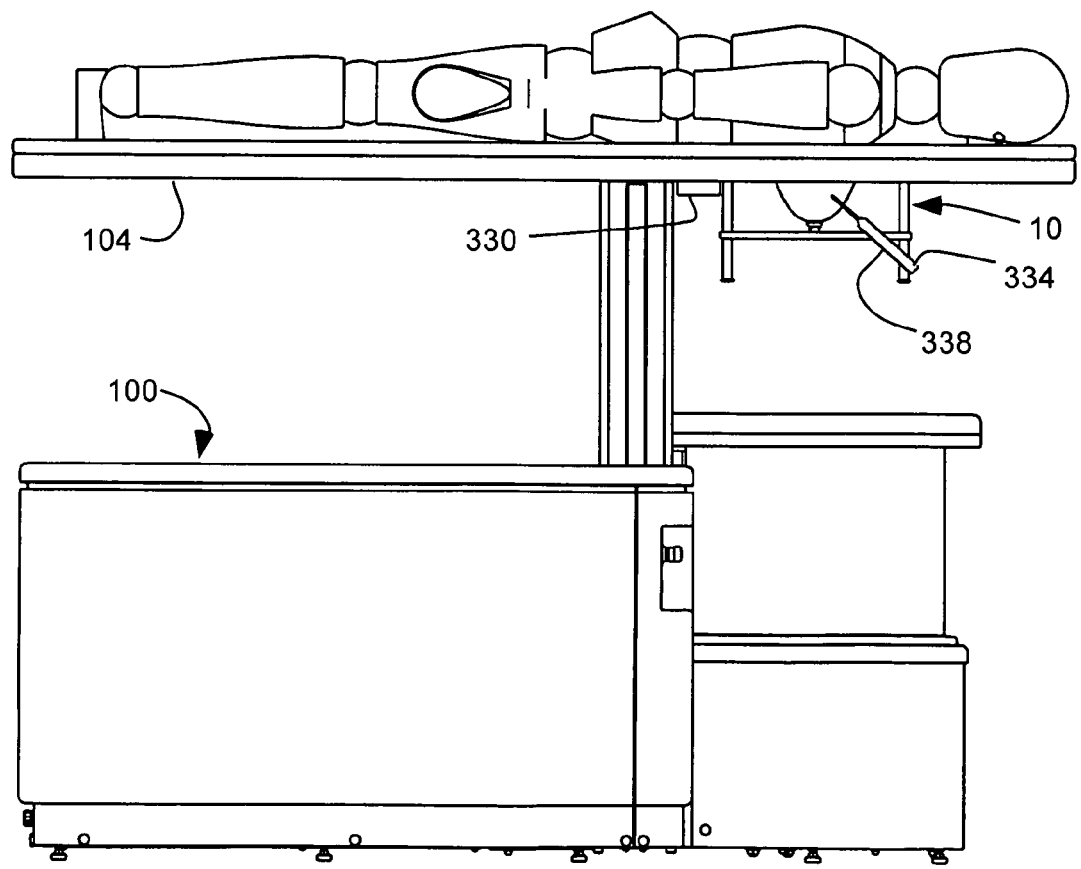
FIG. 4a is a side view of the scanning system of FIG. 1 with an electromechanical navigation system and a treatment instrument in accordance with an aspect of the present invention.

Referring to FIG. 4*a*, the navigation system can use an electromagnetic signal system. For example, a transmitter 330 can be attached to the system at a known location with respect to the frame, and thus the breast and tumor, such as on a lower surface of the table adjacent the frame. One or more receivers 334 can be disposed on a treatment instrument 338. Thus, the receivers 334 can receive or sense a signal from the transmitter to determine the position of the treatment instrument 338 with respect to the transmitter, and thus the breast and the tumor. In addition, one or more reference receivers can be disposed on the breast, the table or the frame to position the breast, table or frame. Furthermore, the system can be calibrated by touching the treatment instrument at known locations, such as the frame or other point. Alternatively, one or more transmitters can be disposed on the treatment instrument and a receiver can be disposed on the table.

Figure 5:
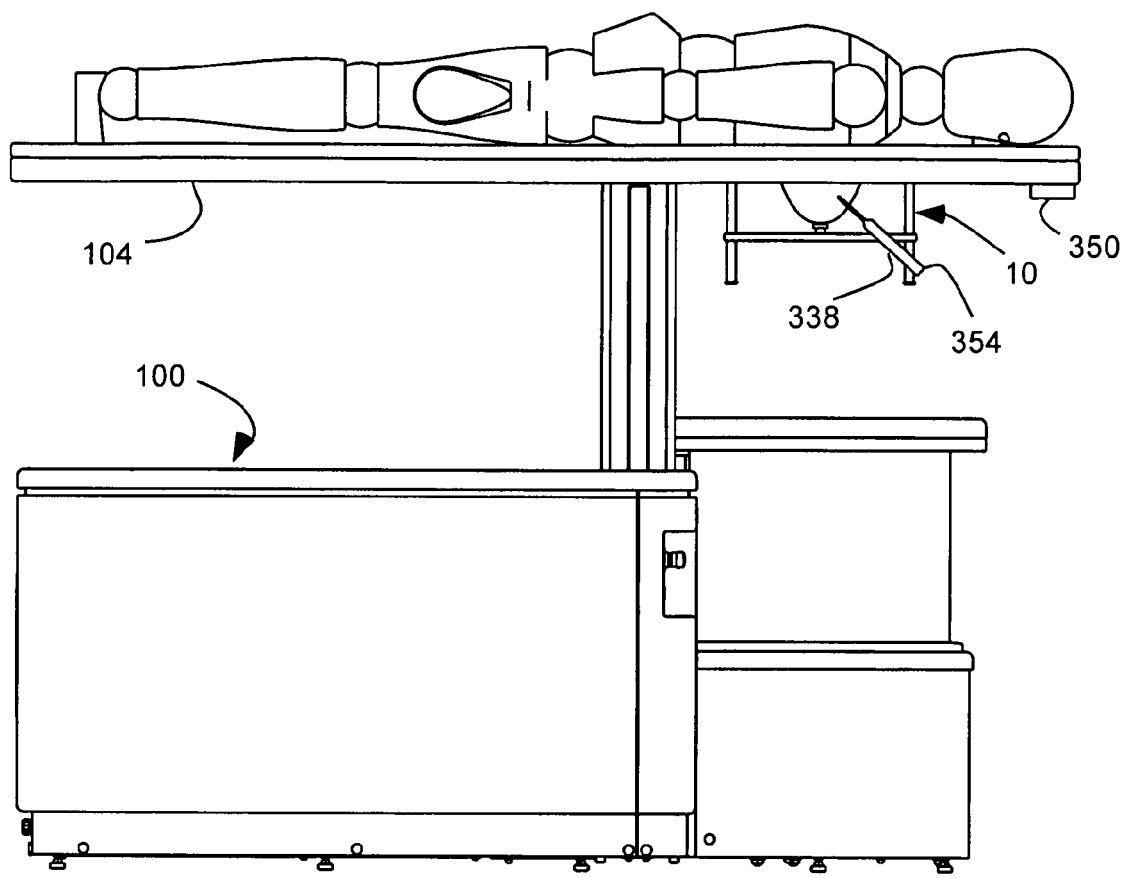
FIG. 5 is a side view of the scanning system of FIG. 1 with a camera navigation system and a treatment instrument in accordance with an aspect of the present invention.

Referring to FIG. 5, the surgical navigation system can use an infrared camera or the like. For example, a camera 350 can be attached to the system at a known location with respect to the frame, and thus the breast and tumor, such as on a lower surface of the table adjacent the frame. One or more infrared markers or "dots" 354 can be disposed on a treatment instrument 338. Thus, the camera 350 can see or sense the dots 354 to determine the position of the treatment instrument 338 with respect to the camera, and thus the breast and the tumor. In addition, one or more reference dots can be disposed on the breast, the table or the frame to position the breast, table or frame. Furthermore, the system can be calibrated by touching the treatment instrument at known locations, such as the frame or breast magnet.

As described above, the further treatment can include biopsy, marker placement, therapy or surgery, and the treatment instrument 300 or 338 can be a biopsy device, a marker placement device, a needle, a probe or a surgical instrument. The treatment instrument can be a biopsy device that can be used to obtain a tissue sample of the tumor. For example, a needle can be used to obtain a tissue sample. The treatment instrument can be a marker placement device that can be insertable into the breast and capable of inserting at least one marker at the margins of the tumor. Such markers can be wires, dye, or clips. For example, a needle can be used to place markers. A syringe can be filled with a visible dye that would be injected using stereotactic guidance in small "spots" immediately prior to excisional surgery. This dye could also contain components that would allow it to be imaged ultrasonically in order to check the position of the "spots" by scanning as described above.

Figure 6A:
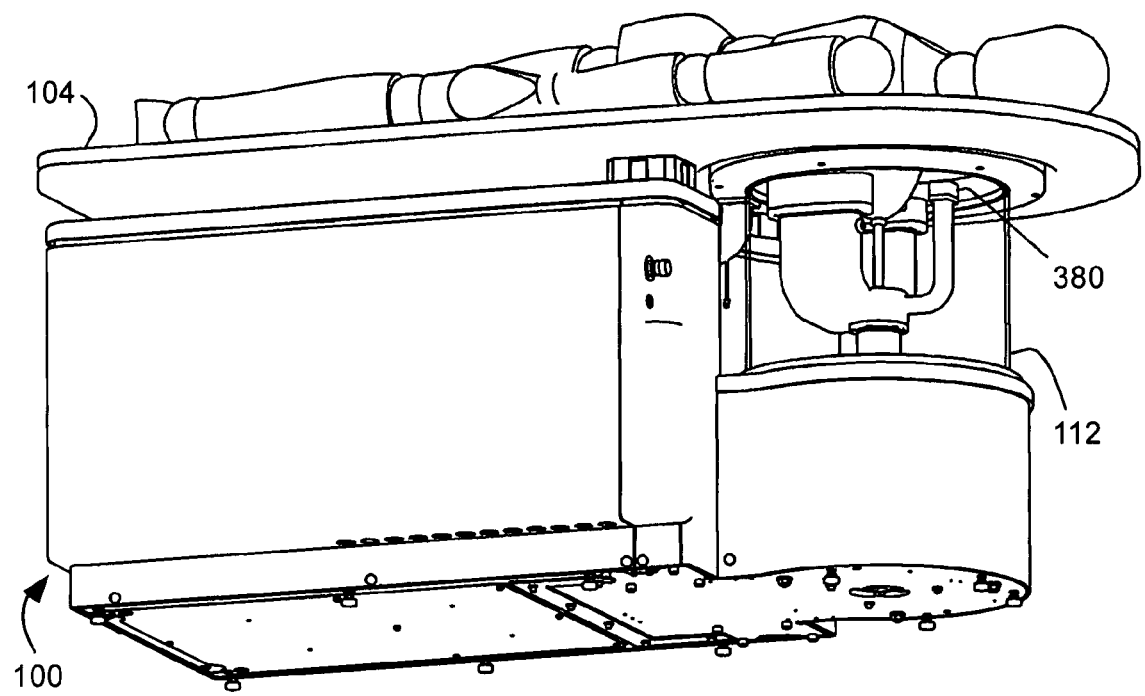
FIG. 6a is a perspective view of the scanning system of FIG. 1 with an ultrasonic emitter in accordance with an aspect of the present invention.
Figure 6B:
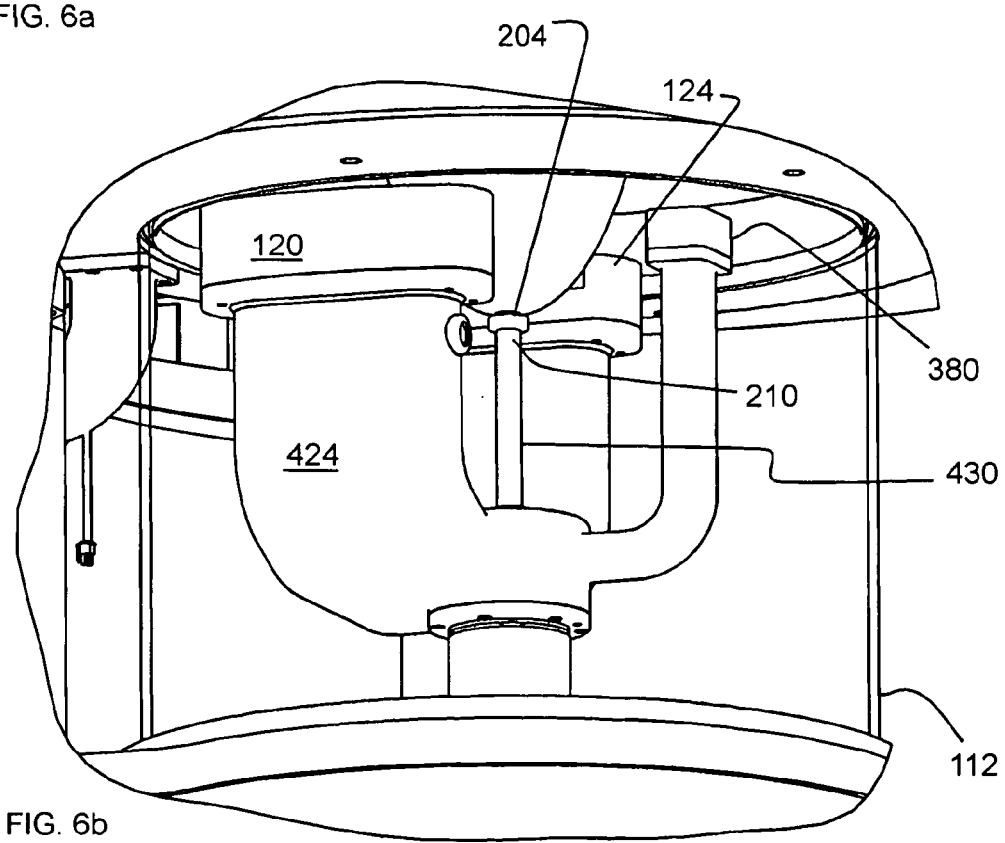

Referring to FIGS. 6*a* and 6*b*, therapy can include ultrasound ablation and the treatment instrument can be an ultrasound emitter 380 capable of producing ultrasound energy directable to a tumor in the breast. The ultrasound emitter 380 can be coupled to the ultrasound transducers 120 and 124, and can be operated in the bath, using the medium to transmit the ultrasound energy to the breast and the tumor. Alternatively, the ultrasound emitter can be coupled to the frame. Alternatively, an ultrasound emitter can be positioned against the breast while the breast is out of the bath and table elevated (represented by 300 in FIGS. 1*a-d*).

Therapy can include a thermal probe with a hot tip or a cold tip insertable into the breast. The thermal probe (represented by 300 in FIGS. 1*a-d*) can be coupled to the frame.

Figure 7A:
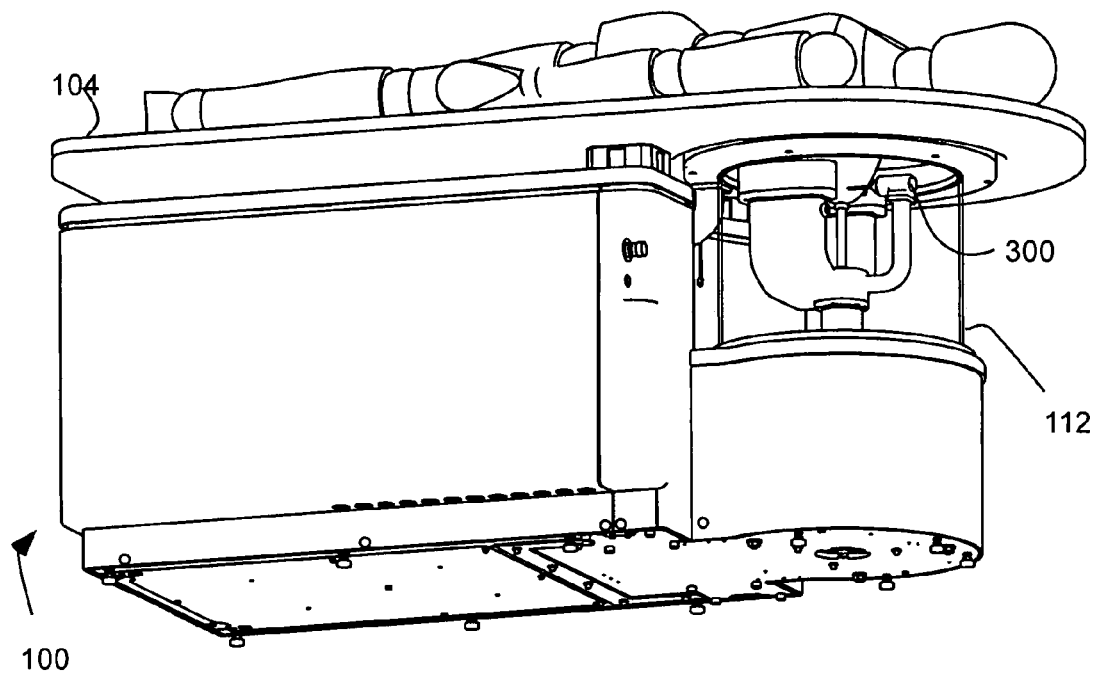
FIG. 7a is a perspective view of the scanning system of FIG. 1 with a treatment instrument in accordance with an aspect of the present invention.
Figure 7B:
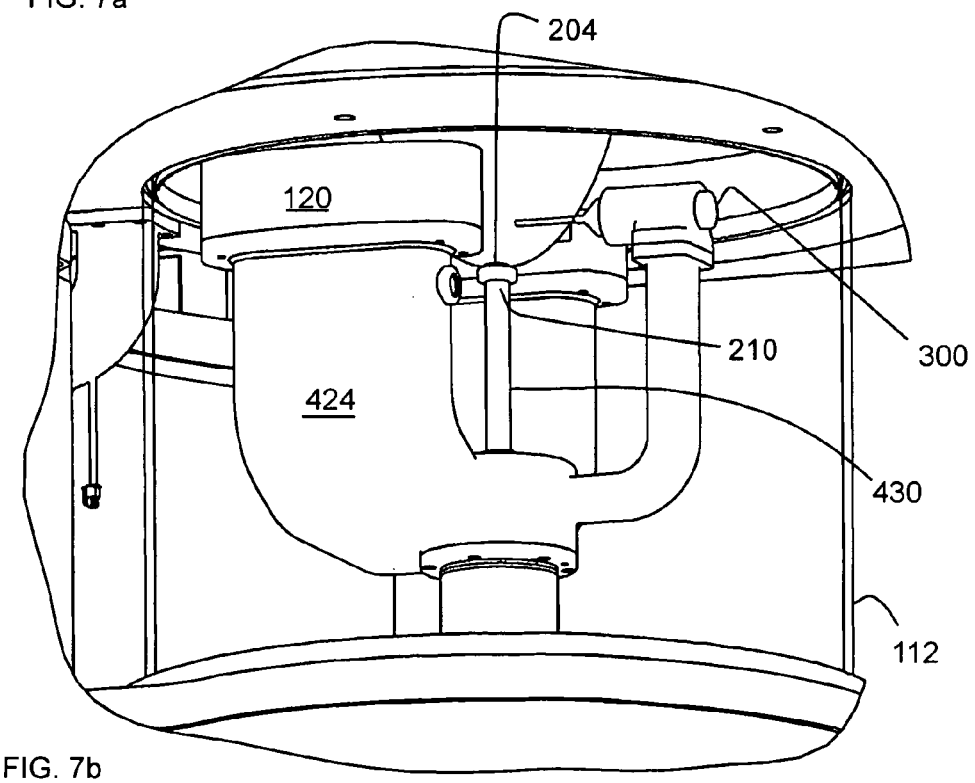
Figure 8A:
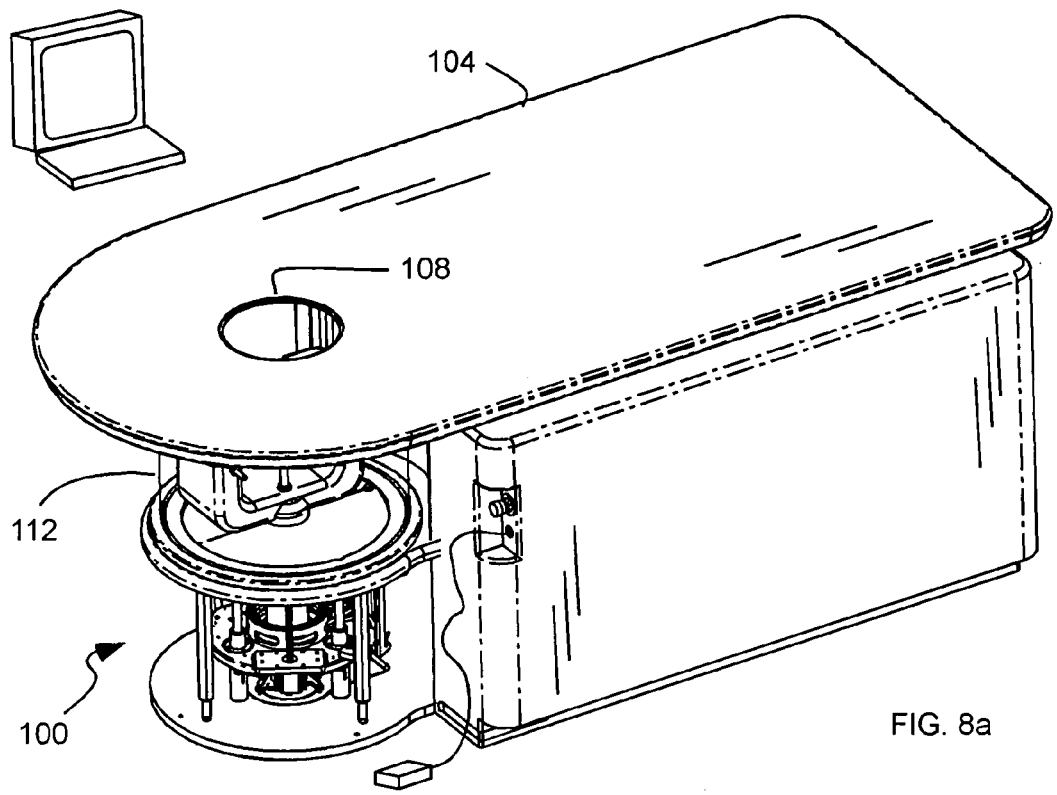
FIG. 8a is a perspective view of the scanning system of FIG. 1.
Figure 8B:
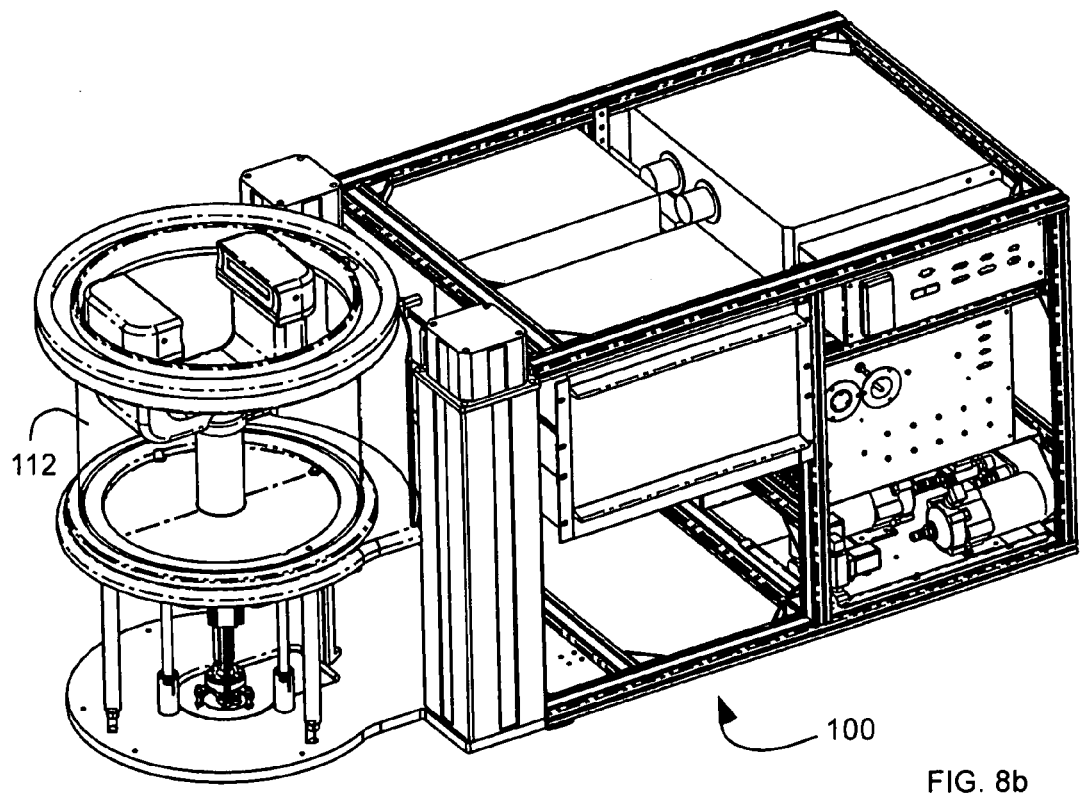
Figure 8C:
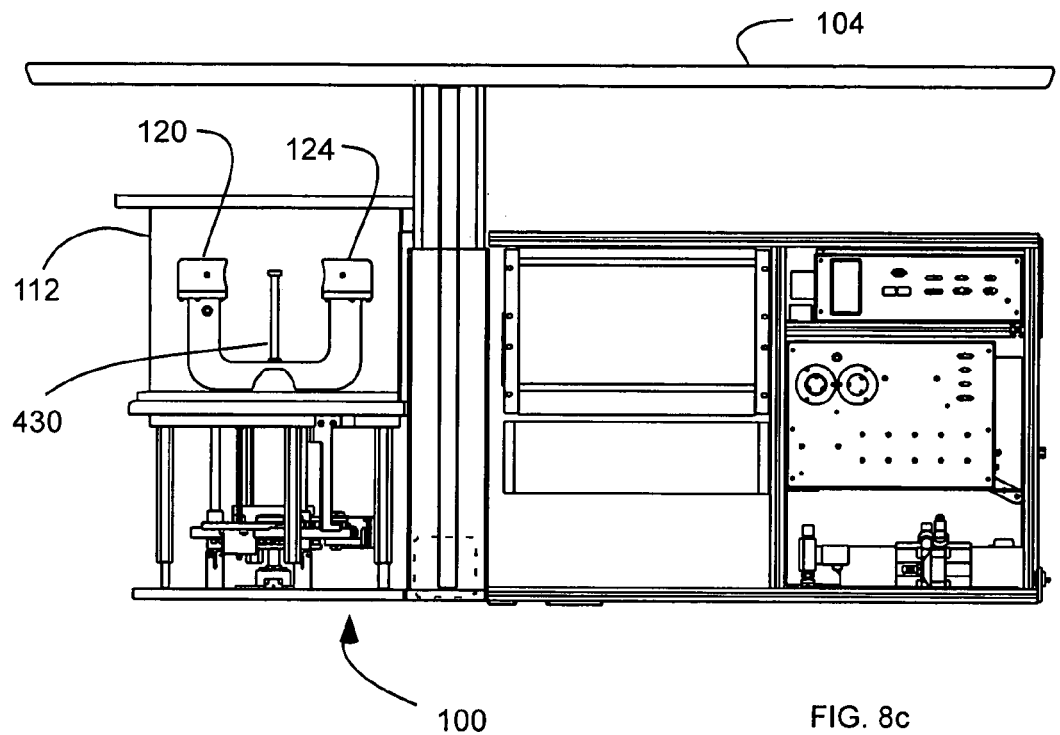
FIG. 8c is a cross-sectional side view of the scanning system of FIG. 8a with the table in a raised configuration.
Figure 8D:
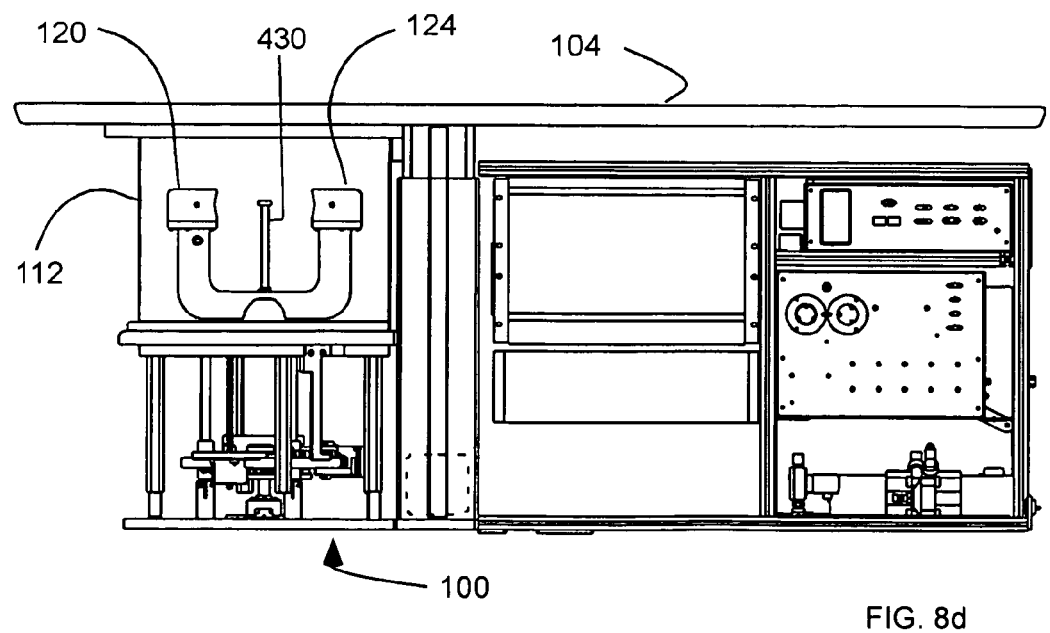
FIG. 8d is a cross-sectional side view of the scanning system of FIG. 8a with the table in a lowered configuration.

Referring to FIGS. 7*a* and 7*b*, the treatment instrument 300 can be disposed in, and operated in, the bath 112. Again, the treatment instrument 300 represents a biopsy device, a marker placement device, a needle, a probe or a surgical instrument.

A method for using the system 100 and the frame 10 described above, and for imaging and treating a breast of a patient, includes disposing the breast 116 into a bath 112 of medium. The patient can be positioned on the table with the breast pendent through the aperture 108 in the table. The breast 116 is physically secured and maintained in a repeatable position and in a repeatable shape with respect to a chest wall of the patient. For example, a breast magnet 204 can be secured to the breast, and can engage a bath magnet 210 disposed on a rod in the bath, as described below. The breast is scanned with ultrasound signals from transducer arrays 120 and 124 to create a three-dimensional image or model of the breast, and to locate a position of a tumor or a lesion in the breast with respect to the three-dimensional image or model. The tumor or lesion is further treated while maintaining the position and the shape of the breast with respect to the chest wall of the patient as during scanning. Maintaining the position and the shape of the breast allows the image or model of the breast created from ultrasonic scanning to correspond substantially to the actual position and shape of the breast during treatment where the image or model is used for guiding a treatment instrument. The patient can be maintained on the table 104 with the breast pendent through the aperture 108 while the tumor or the lesion is further treated.

Maintaining the position and the shape of the breast can include securing the breast 116 to the frame 10 suspended from the table 104 supporting the patient. As described above, the breast magnet 204 secured to the breast can engage the frame magnet 208 on the frame.

It will be appreciated that further treating the breast can be facilitated by removing the breast from the bath for the further treatment. For example, the table 104 can be elevated, thus elevating the breast from the bath. The position and the shape of the breast can be substantially maintained with respect to the chest wall of the patient out of the bath as in the bath during scanning using the frame. The frame 10 can be suspended from the table 104 after the breast is removed from the bath, and after the table is elevated. Then the breast can be secured to the frame.

As stated above, a biopsy can be performed by inserting a biopsy device (represented by 300 in FIGS. 1*a-d*) into the tumor or lesion and removing a tissue sample. The biopsy device can be guided by a navigation system linked to the three-dimensional image or model of the breast. The navigation system can mechanically linked to the image or model using the frame 10 as a stereotactic frame. Alternatively, the navigation system can use an infrared camera 350 (FIG. 5) visually sensing an infrared marker or dot on the biopsy device (represented by 338 in FIG. 5). In addition, an infrared reference marker can be disposed on the breast, the frame, or the table. Alternatively, the navigation system can use an electromagnetic transmitter and receiver system coupled to the biopsy device (represented by 330 in FIG. 4a). In addition, the transmitter and receiver system can be coupled to a reference on the breast, the frame, or the table. Furthermore, one or more markers can be inserted into the breast using the biopsy device to mark a margin of the tumor to guide a surgeon during surgery to remove the tumor.

As stated above, ultrasound ablation can be performed by directing ultrasound energy at the tumor. An ultrasound emitter 380 (FIGS. 6a and 6b) can be coupled to the ultrasound transducers 120 and 124 and can be operable in the bath with the ultrasound energy transmittable through the medium. The breast can be disposed back into the bath of medium while substantially maintaining the position and the shape of the breast with respect to the chest wall of the patient as during scanning, prior to performing ultrasound ablation, as shown in FIGS. 6a and 6b. Thus, the breast magnet can be reconnected to the bath magnet, as described below. In addition, an ultrasound activated drug can be injected into the patient. Ultrasound energy from the emitter can activate the drug, while directing the ultrasound energy can limit activation to the tumor. The ultrasound emitter can be directed using a navigation system as described herein.

A drug, such as a chemotherapy drug, can be injected into the tumor using a needle (represented by 300 in FIGS. 1a-d, or 338 in FIGS. 4a and 5). The needle can be coupled to the frame. In addition, the needle can be guided by a navigation system as described herein.

As stated above, the tumor can be thermally treated by inserting a probe (represented by 300 in FIGS. 1a-d, or 338 in FIGS. 4a and 5) with a hot tip or a cold tip into the tumor. The probe can be coupled to the frame. In addition, the probe can be guided by the navigation system as described herein.

As stated above, one or more markers can be inserted into the breast to mark the margins of the tumor to guide a surgeon during surgery to remove the tumor. The markers can be inserted by a marker insertion device (represented by 300 in FIGS. 1a-d, or 338 in FIGS. 4a and 5), such as a needle. The markers can be wires, dye, or clips.

As stated above, surgery can be performed to remove the tumor using a surgical instrument (represented by 300 in FIGS. 1a-d, or 338 in FIGS. 4a and 5). The surgical instrument can be guided by a navigation system linked to the three-dimensional image or model of the breast. The navigation system can be mechanically linked to the image or model using the frame 10 as a stereotactic frame. Alternatively, the navigation system can use an infrared camera 350 (FIG. 5) visually sensing an infrared marker or dot on the surgical instrument (represented by 338 in FIG. 5). In addition, an infrared reference marker can be disposed on the breast, the frame, or the table. Alternatively, the navigation system can use an electromagnetic transmitter and receiver system coupled to the surgical instrument (represented by 330 in FIG. 4a). In addition, the transmitter and receiver system can be coupled to a reference on the breast, the frame, or the table.

Alternatively, the breast can remain in the bath during further treatment, as shown in FIGS. 3a and 3b. A treatment instrument 300 can operate in the bath.

The system can be a non-invasive, diagnostic tool to provide detailed information about the physiology (i.e. bulk tissue properties) and anatomy (i.e. physical architecture) of the breast. The system can be used as an adjunct to mammography to aid physicians in diagnosing breast cancer by providing information about tissue properties that help to more clearly differentiate normal or benign from malignant tissue in the breast. The system can replace other diagnostic testing, such as diagnostic mammograms, breast ultrasound, and other imaging technologies currently used between a screening mammogram and a biopsy.

In general, the system 100 can use ultrasound inverse scattering technology to produce a 3-D stack of tomography (2-D planar slice) images (similar in appearance and spatial resolution to CT or MR imaging methods). Direct 3-D imaging is a further feature of the system 100. These images can be produced using two different techniques, namely Ultrasound Reflective Tomography (URT) and Ultrasound Inverse Scattering Tomography (UIST). Compared with conventional projection mammography, URT images can be more detailed, easier to read, and do not use potentially harmful ionizing radiation. Unlike conventional ultrasound, ultrasound images using inverse scattering technology completely penetrate and sample the entire breast for uniformity and better overall resolution. In addition, such images are quantitative representations of ultrasound tissue properties, and therefore are not dependent on the system operator for image quality and consistency. The images can be reconstructed in three dimensions providing an important visualization tool for diagnosis, biopsy and surgery staging.

The system 100 can use two ultrasound arrays that rotate around the breast, generating true 3-D images and diagnostic information in a commercially viable timeframe, such as less than 20 minutes per exam. The breast can be disposed in a bath 112 of medium, such as liquid, water or gel. The use of water will be described throughout for illustrative purposes.

The system 100 can include two opposing ultrasound transducer arrays 120 and 124 movably disposed in the bath 112 to obtain both reflection and transmission information used to generate images and diagnostic information. The arrays 120 and 124 are mechanically designed to rotate and move up and down generating a complete 3-D data set for the area of interest or even for the entire breast. Ultrasound pulses can be used for two imaging modalities: reflective and transmissive. For reflective images, the system emits a pulse from one array and receives the reflected energy back in the same array. The array can emit a pulse at 20 positions (every 18 degrees) around the breast. During the same rotation sequence, the transmitting array can emit an ultrasound signal into and through the breast at 180 different locations (every 2 degrees) around the entire breast. The resulting waveforms are received by the opposing array. This allows the system to simultaneously generate data for both reflection and transmission sound properties of the breast. Alternatively, the arrays can move and/or emit continuously. The arrays 120 and 124 are one example of means for transmitting and receiving ultrasound signals in the bath. Other means for transmitting and receiving ultrasound signals in the bath include, for example, ring arrays, a tank lined with arrays, etc.

The imaging system produces three separate images using two different imaging techniques: 1) transmission information generates images representing bulk tissue properties of speed of sound and attenuation of sound at each point in the breast; and 2) data generated from reflection information generates detailed reflective tomographic images that are refraction corrected. These imaging techniques are combined to effectively produce a three-dimensional stack of "slices" of the breast. Data from the ultrasound source is analyzed, and a quantitative map of tissue properties is rendered. In the "transmission mode" the energy propagates through the breast (or other soft tissue). In the "reflection mode", the energy reflects back to the receivers. In both cases, the energy of the acoustic wave is refracted and scattered from the tissue it encounters. In this process multiple physical phenomena take place: reflection, refraction, diffraction, and multiple scattering events. These effects are generally ignored in present ultrasound, which seriously degrades the image, therefore rendering it useful only in differentiating architectural or structural properties within the breast. In present ultrasound it is impossible to acquire quantitative values at a level sufficient for diagnosis of tissue characteristics using standard reflection ultrasound or imaging.

Further details of inverse scattering technology and imaging are disclosed in U.S. Pat. Nos. 4,662,222; 5,339,282; 6,005,916; 5,588,032; 6,587,540 and 6,636,584, which are herein incorporated by reference in their entirety.

The transducer arrays 120 and 124 can be disposed in the bath 112, and carried by an armature 424, also disposed in the bath 112. The armature 424 can include a u-shaped member disposed on a vertical column that extends through a bottom of the bath. Each vertical arm of the u-shaped member can carry one of the arrays. The u-shaped member can be sized to position the arrays around the breast. The arrays 120 and 124 can be rotatable around an axis of rotation, and displaceable vertically. For example, the armature can rotate around the vertical column, thus rotating the arrays. A rotational motor can be coupled to the armature 424 to rotate the armature. For example, the rotational motor can be a rotational step motor coupled to the armature or vertical column by a belt. In addition, a linear motor can be coupled to the armature to linearly displace the armature, and thus the transducer arrays. For example, the vertical column can be carried by a platform on a plurality of rods. One of the rods can be threaded. The linear motor can engage the threaded rod such that rotation of the motor can raise and lower the platform, and thus the vertical column along with the rotational motor. A rotational and/or sliding seal can be formed between the bath and the armature, or vertical column, to seal the bath where the armature or vertical column passes through the bottom of the bath. In addition, one or more bearings or rotational bearings can be disposed between the vertical column and the platform to facilitate rotation and reduce frictional forces. Thus, the platform can carry the armature and related motors to move the armature.

The transducer arrays 120 and 124 can be off-set, or non-concentric, with respect to an axis of rotation. The armature 424 can also be offset or non-concentric with respect to the axis of rotation.

The transducer arrays 120 and 124 can send and receive ultrasound signals at a plurality of elevational locations along the breast, and at a plurality of rotational orientations around the breast at each elevational location. The linear motor can move (raise or lower) the transducer arrays sequentially through a plurality of different elevational locations along the breast. The rotational motor can sequentially move (or rotate) the transducer arrays through a plurality of different angular orientations around the breast at each elevational location. As described above, arrays can emit a pulse at 20 positions (every 18 degrees) around the breast. During the same rotation sequence, the transmitting array can emit an ultrasound signal into and through the breast at 180 different locations (every 2 degrees) around the entire breast. The resulting waveforms are received by the opposing array. The arrays can then be moved to a different location along the breast and the sequence repeated. Alternatively, the arrays can emit during a continuous motion. Thus, the movement of the arrays and armature can be discrete, or stepwise through discrete position, or continuous.

In addition, the arrays 120 and 124 can be tilted, or rotatable to have tilted orientation to allow imaging closer to the chest wall. For example, the arrays can be angled or directed in an upwardly angled direction so that the arrays emit upwardly at an angle and receive downwardly at an angle.

Alternatively, transducers can be configured or arrayed differently to have different movement, or even no movement. For example, transducers can be vertically oriented along the length of the breast, and can be rotated around the breast, without the need to move the transducers vertically. Alternatively, transducers can be horizontally oriented around the circumference of the breast, and can be moved vertically along the length of the breast, without the need to rotate the transducers. Furthermore, the transducers can be disposed around the breast, and along the length of the breast, so that the transducers do not have to be moved or rotated.

The bath 112 can be cylindrical and transparent, or can have a bath wall that is cylindrical and transparent. The bath can be any desired shape, but cylindrical is believed to be the most efficient because it matches or allows the rotational motion of the arrays while minimizing volume. The transparent wall allows the breast to be viewed during the scan, and allows a technician to observe operation of the armature. Alternatively, the bath wall can be opaque or translucent, and can have a window formed therein. The bath can include one or more holes therein forming inlet and/or outlet openings to allow fluid to enter and/or exit the bath. An upper end of the bath can be open to receive the breast, as described in greater detail below.

The bath 112 can be supported by or disposed on a base. The base can include a framework and can contain various components of the system, as described in greater detail below. A skin or skirt can be disposed around the base, or portions thereof, to protect and restrict access to the various components. The bath 112 can be disposed at one end of the system or base to increase the viewing angle or viewing perimeter. The base can include controls, such as an emergency shut-off or stop button. In addition, the base can include various input/output connections, such as for controls.

A horizontal table 104 can be disposable over the bath 112 and the base to receive the patient thereon. The table 104 can be rigid, but can have a padded upper surface for patient comfort. The table 104 can be supported or carried by the base. An aperture 108 can be formed in the table 104 and positionable over the bath 112. In use, the patient's breast is received pendent through the aperture, and into the bath. The aperture 108 can be located nearer one end of the table. The end of the table with the aperture can be broadly curved to circumscribe the bath and/or the aperture. The curved end of the table facilitates access to the bath and/or breast, and facilitates viewing the bath and/or breast.

Figure 1D:
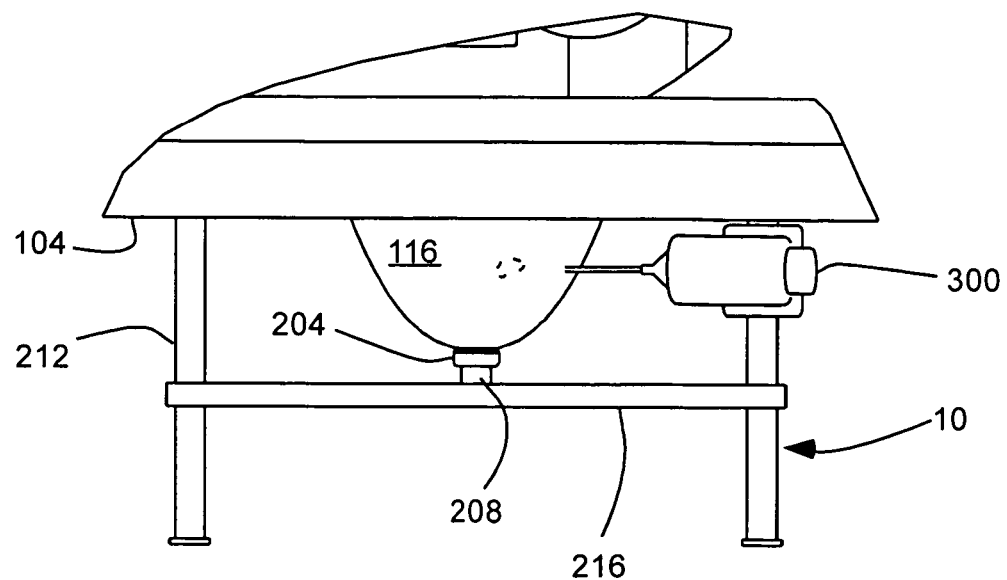
FIG. 1d is a partial side view of the frame of FIG. 1.
Figure 2A:
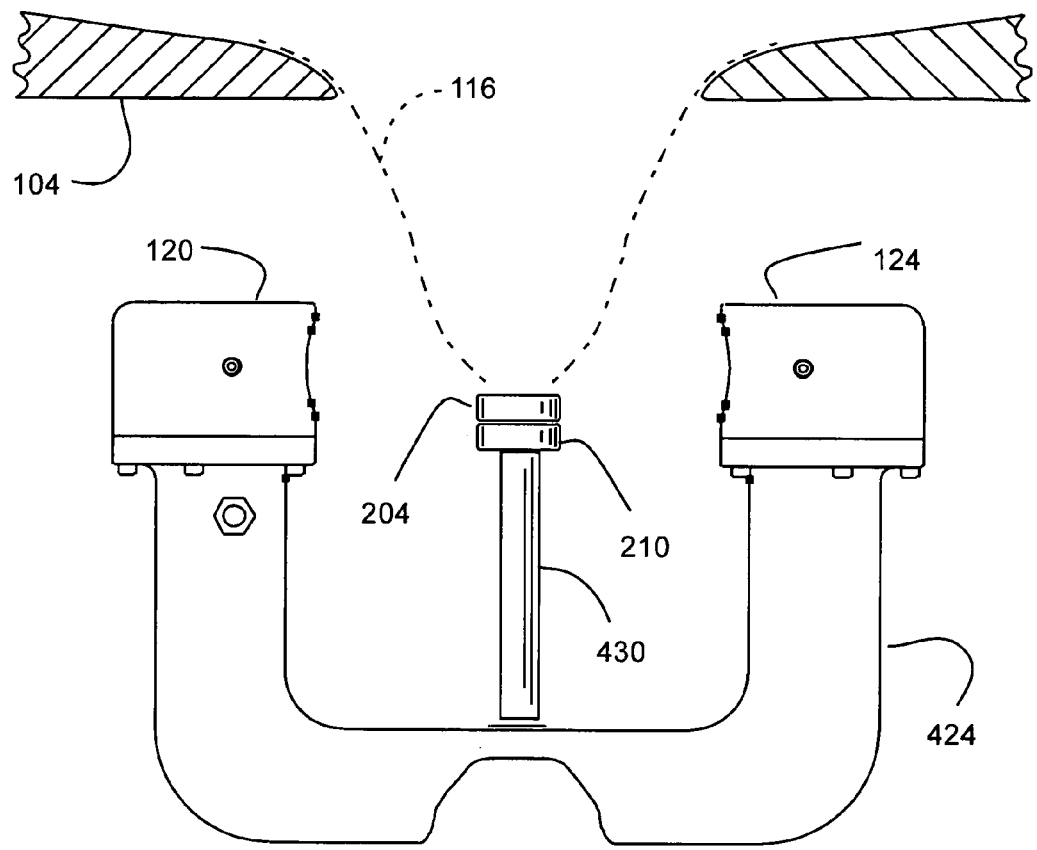
FIG. 2a is a side schematic view of the scanning system of FIG. 1 with the breast physically secured and maintained in a repeatable position and in a repeatable shape.
Figure 2B:
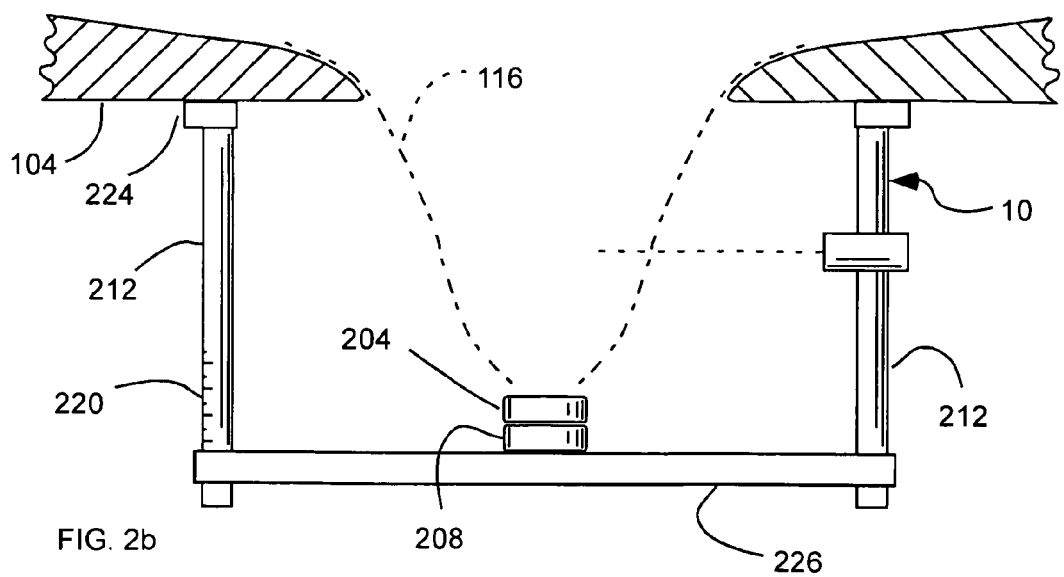
FIG. 2b is a side schematic view of the frame of FIG. 1 with the breast maintained in the position and the shape as during scanning.

The table 104 and the bath 112 can be linearly vertically displaceable with respect to one another. For example, the table 104 can be movable upward and downward, away from and towards the bath. The table 104 can have a lowered position, as shown in FIGS. 1b and 1d, and a raised position, as shown in FIGS. 1a and 1c. In the lowered position, the table 104 is adjacent the bath to position the breast within the bath. In the raised position, the table 104 is spaced-above the bath to elevate the breast above the bath. The raised position allows access to the breast by a technician or physician. For example, a technician can center the breast in the aperture, and/or draw the breast further through the aperture.

One or more columns can support the table. For example, a pair of columns can be disposed on each side of the base. One or more motors can be coupled to the columns to raise and lower the columns, and thus the table. The motors can be located within the columns, and can be rotational motors providing relative rotational movement between a threaded screw and a threaded nut to provide linear motion. The column(s) and motor are one example of means for maintaining the table in the raised position with the table spaced-above the bath, and means for raising and lowering the table.

The table can also be displaceable horizontally, as shown in dashed lines, so that the aperture can be displaced away from the bath to allow further access to the breast for additional procedures, such as biopsies. For example, the table can be linearly displaceable, such as longitudinally in a forward direction. A linear slider can be disposed between the columns and the table to allow the table to slide. As another example, the table can be rotationally or pivotally disposed on the base. A rotational bearing can be disposed between the columns and table to allow the table to pivot or rotate.

As discussed above, the bath 112 contains a medium, such as liquid or water. The liquid or water can have characteristics, such as purity and the like, to facilitate transmission of the signals from the arrays, or to resist interference with such transmission. For example, the liquid or water can be purified, filtered, de-ionized, degassed, etc. In addition, the liquid or water can have known qualities, such as temperature, to facilitate data calculations or conversions, and to provide patient comfort. For example, the liquid or water can have a temperature similar to normal body temperature (or approximately 30° C.).

A breast retention assembly can be used to secure the breast within the bath. For example, a pair of magnets, including a breast magnet 204 attached to the breast and a bath magnet 210 (FIGS. 2a, 6a-7b and 9b) disposed in the bath, can be used to hold the breast. The breast magnet 204 can have a breast connector to secure the breast magnet to the breast of the patient. The breast connector can use an adhesive similar to that used to secure other medical sensors to the skin. The bath magnet and the breast magnet magnetically couple when the table is in the lowered position. A beveled cup can be associated with one of the breast or bath magnets, such as the bath magnet, to center the breast and bath magnets with respect to one another. The beveled cup can be plastic and can mechanically center the magnets. The bath magnet 210 can be movable within the bath, and can be vertically moved between a raised and a lowered position. The raised position of the bath magnet can correspond to the raised position of the table, and can allow a technician to secure the bath and breast magnets prior to lowering the table and immersing the breast in the bath. The bath magnet 210 can be disposed on and carried by a rod 430 (FIGS. 2a, 6a-7b and 9b) vertically movable within the bath. The rod 430 can extend through a hollow interior of the armature, or vertical column thereof. A seal can be formed around the rod.

The rod 430 can be raised and lowered by a motor, such as a stepper motor. The stepper motor can be rotational and can cause relative rotation between a threaded rod and nut to raise and lower the rod. The stepper motor can indicate the position of the rod to control electronics, and thus the tip or nipple of the breast. Similarly, the position of the table can be determined using the motors. Thus, the length and position of the breast can be determined. Alternatively, sensors can be used.

The magnets and/or rod are one example of means for securing the breast within the bath. Other means for securing the breast within the bath can include, for example, attaching a shaft, wire, spring, weight, magnet, or the like at or near the nipple. As another example, means for securing the breast within the bath can include a retention device mounted to the table permitting the ultrasound tank to be lowered out of the way (or the patient raised) with the breast remaining in a known position for stereotaxic guided biopsy or other medical procedures. The retention device can include a frame rotatably mounted to the table. The frame can include a ring circumscribing the hole and rotatably coupled to the table by a bearing. A pair of posts can extend downwardly from the ring to a cross-member can extend between the posts. A magnetic coupling can include a frame magnet pivotally coupled to the cross-member or brace by bearings, and a nipple or breast magnet coupled to the patient's breast or nipple, and magnetically coupled to the frame magnet. The bearings allow the frame, or posts and cross-member to rotate about the breast, thus rotating out of interference with the arrays during operation, and without twisting the patient's breast. The frame can be pivoted when abutted by the arrays. Alternatively, magnets can be disposed between the brace and arrays to resist interference between the two.

As another example, means for securing the breast within the bath can include a special bra or other membrane could be could be worn over the breast to help hold the breast in position. The bra could include a device for attaching a shaft, wire, spring, weight or magnet as described above. A membrane can be provided in the shape of a cone to receive the breast therein. The membranes can include a proximal, larger opening to receive the breast, and a distal smaller opening through which suction can be applied to draw the breast into and against the membrane. An ultrasound gel can be disposed between the breast and the membrane for lubrication and coupling.

A light source, such as a laser pointer, can project a light beam (such as a fan beam) onto the breast at an area of interest. The area of interest can be marked prior to immersing the breast into the bath. The area of interest can be determined beforehand by reference to breast examinations, mammograms, etc. The laser pointer can be mounted to the armature, and be positioned at the arrays. Thus, the armature and arrays can be raised or lowered until the light beam from the laser pointer aligns with the mark on the breast corresponding to the area of interest. This position can be saved in the system as a center of the area of interest, and the scan can begin and end at a predetermined distance above and below the center of interest. It will be appreciated that the position of the armature, and thus the arrays, can be determined from the motors used to position the armature, or from other sensors.

In addition, a camera can be positioned to provide an image of the breasts and arrays. The camera can be coupled to the system and/or a display or control module associated with the system. The camera can be mounted on the armature and positioned at the arrays. A horizontal line, or cross-hair, can be provided on the display, camera, or system to align the camera, and thus the arrays, with the mark on the breast corresponding to the area of interest. The camera can also include a light source, such as one or more LEDs.

Figure 9A:
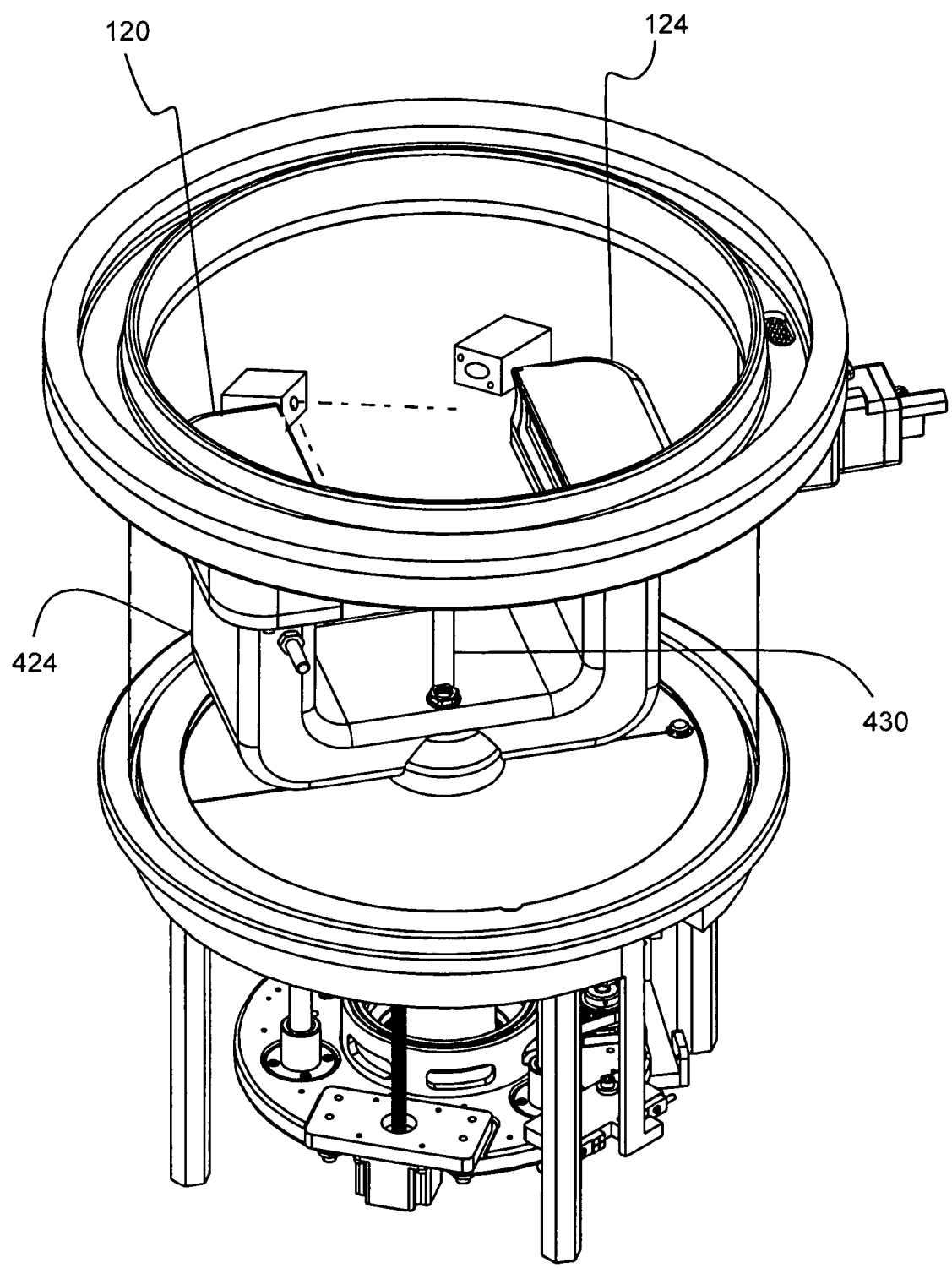
FIG. 9a is a perspective view of a bath of the scanning system of FIG. 1.
Figure 9B:
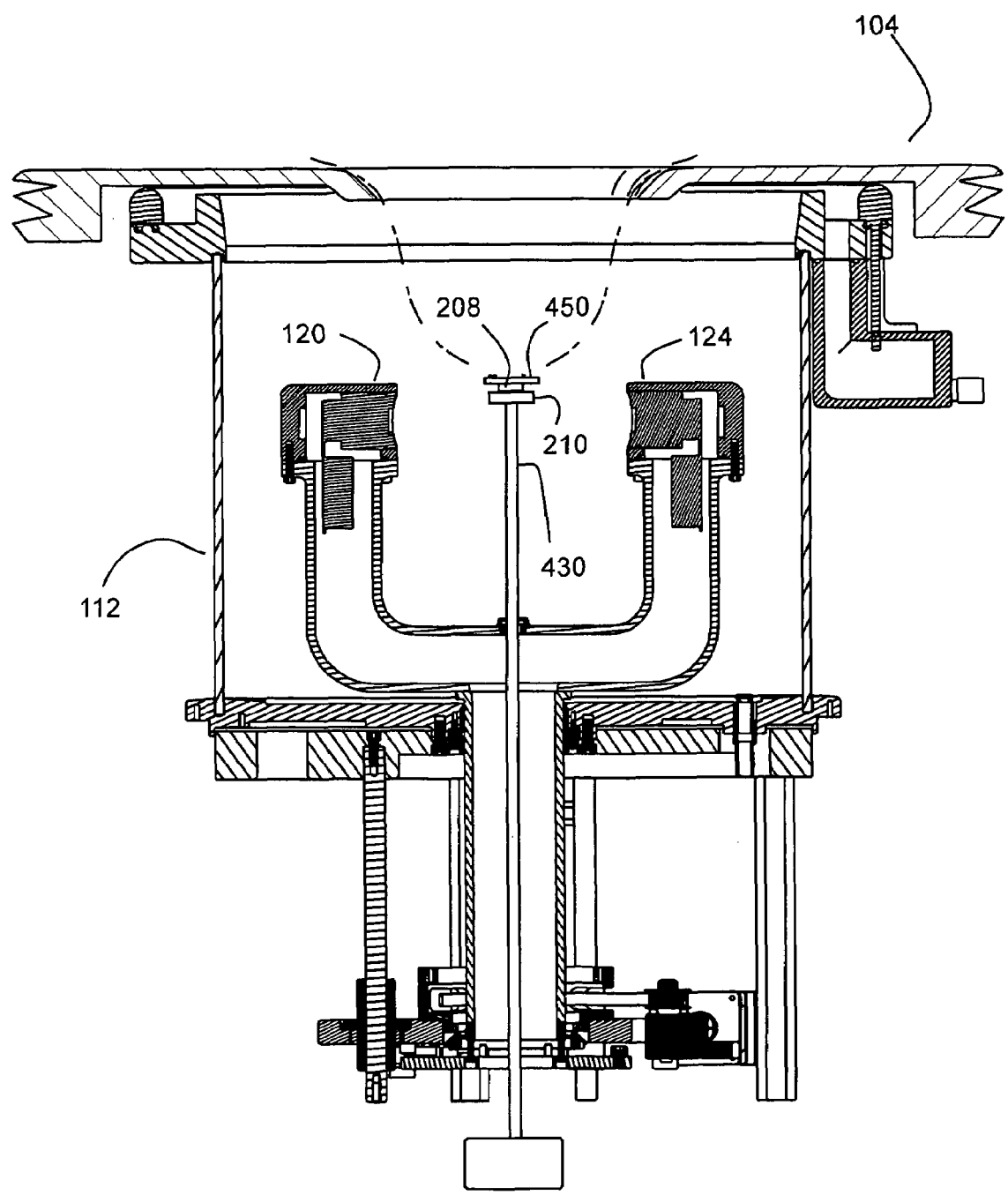

A method for preparing a breast of a patient for scanning can include cleaning and drying a portion of the breast, such as the nipple. The breast magnet 204 can be secured to the breast with the breast connector 450 (FIG. 9b). In addition, an area of interest can be identified and marked on the breast.

The patient can be positioned on the horizontal table 104. The table can be initially positioned at the lowered position, and raised after the patient is on the table. The table can then be raised. Thus, the table can be initially raised to a higher elevation and subsequently lowered to a lower position. The breast can be disposed through the aperture 108 in the table. The gap between the table and the bath in the raised position allows the technician to center and pull the breast through the aperture. The table 104 can be displaced linearly vertically towards the bath to immerse the breast into the water.

After the breast is immersed in the bath, the breast is secured within the bath. The rod 430 can be raised until the bath magnet 210 docks with, or magnetically couples to, the breast magnet 204. The beveled cup can assist in centering the magnets, and thus the breast. In addition, the rod 430 and the bath magnet 210 can be lowered to pull on and exert a degree of tension to the breast. Alternatively, the bath magnet can be coupled to the breast magnet prior to the breast being immersed within the bath. Thus, the table and rod can be lowered together into the bath. A length of the breast can be determined based on the position of the rod and the position of the table.

The arrays can be positioned so that a beam of light from the laser pointer is projected onto the breast at the mark corresponding to the area of interest to be scanned. The position of the arrays can be determined by the system so that the system or technician can determine what portion of the breast to scan. The arrays can be raised or lowered a predetermined amount in order to scan the entire area of interest. Similarly, arrays can be positioned so that the cross-hairs associated with the camera align with the mark.

The arrays 120 and 124 and the armature 424 can initially be in a lowered position. The arrays and armature can be raised and the breast scanned with ultrasound signals from the transducer arrays. As described above, the arrays can send and receive ultrasound signals at a plurality of elevational locations along the breast, and at a plurality of rotational orientations around the breast at each elevational location. Thus, the transducers can be sequentially moved through a plurality of different elevational locations along the breast. In addition, the transducers arrays can be sequentially moved through a plurality of different angular orientations around the breast at each elevational location.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A method for imaging and treating a breast of a patient, comprising:
   a) disposing the breast into a bath with a bath wall and containing a medium;
   b) physically securing the breast and maintaining the breast in a repeatable position and in a repeatable shape with respect to a chest wall of the patient by securing the breast to a frame suspended from a table supporting the patient;
   c) scanning the breast with ultrasound signals from transducer arrays to create a three-dimensional image of the breast and to locate a position of a tumor or a lesion in the breast with respect to the three-dimensional image;
   d) removing the breast from the bath by elevating the table with respect to the bath wall with the frame suspended from the table while maintaining the position and the shape of the breast with respect to the chest wall of the patient as during scanning; and
   e) further treating the tumor or the lesion of the breast.

2. A method in accordance with claim 1, further comprising:
   positioning the patient on the table with the breast pendent through an aperture in the table; and
   maintaining the patient on the table with the breast pendent through the aperture while further treating the tumor or the lesion.

3. A method in accordance with claim 1, further comprising:
   substantially maintaining the position and the shape of the breast with respect to the chest wall of the patient out of the bath as in the bath during scanning.

4. A method in accordance with claim 1, wherein the breast remains in the bath during further treatment, and wherein further treating the tumor or the lesion includes:
   a) performing a biopsy by inserting a biopsy device into the tumor or lesion and removing a tissue sample;
   b) inserting at least one marker into the breast to mark a margin of the tumor using a marker placing device;
   c) performing ultrasound ablation by directing ultrasound energy at the tumor with an ultrasound emitter;
   d) injecting a drug into the tumor using a needle;
   e) injecting an ultrasound activated drug into the patient and directing ultrasound energy at the tumor with an ultrasound emitter to activate the ultrasound activated drug; or
   f) thermally treating the tumor by inserting a probe with a hot tip or a cold tip into the tumor.

5. A method in accordance with claim 3, wherein further treating the tumor or the lesion further includes:
   performing a biopsy by inserting a biopsy device into the tumor or lesion and removing a tissue sample.

6. A method in accordance with claim 3, wherein further treating the tumor or the lesion further includes:
   inserting at least one marker into the breast to mark a margin of the tumor to guide a surgeon during surgery to remove the tumor.

7. A method in accordance with claim 3, wherein further treating the tumor or the lesion further includes performing surgery to remove the tumor using a surgical instrument including:
   a) a stereotactic frame secured to the breast with the surgical instrument attached to the stereotactic frame;
   b) a camera visually sensing an infrared marker on the surgical instrument; or
   c) a transmitter and receiver system coupled to the surgical instrument.

8. A method in accordance with claim 3, wherein further treating the tumor or the lesion further includes:
   performing ultrasound ablation by directing ultrasound energy at the tumor.

9. A method in accordance with claim 3, wherein further treating the tumor or the lesion further includes:
   injecting a chemotherapy drug into the tumor using a needle.

10. A method in accordance with claim 3, wherein further treating the tumor or the lesion further includes:
    injecting an ultrasound activated drug into the patient; and directing ultrasound energy at the tumor.

11. A method in accordance with claim 3, further treating the tumor or the lesion further includes:
    thermally treating the tumor by inserting a probe with a hot tip or a cold tip into the tumor.

12. A method in accordance with claim 5, wherein performing a biopsy includes the biopsy device being guided by a navigation system including:
   a) a stereotactic frame secured to the breast with the biopsy device attached to the stereotactic frame;
   b) a camera visually sensing an infrared marker on the biopsy device; or
   c) a transmitter and receiver system coupled to the biopsy device.

13. A method in accordance with claim 5, wherein performing a biopsy further includes:
   inserting at least one marker into the breast using the biopsy device to mark a margin of the tumor to guide a surgeon during surgery to remove the tumor.

14. A method in accordance with claim 8, wherein performing ultrasound ablation further includes:
   disposing the breast back into the bath and substantially maintaining the position and the shape of the breast with respect to the chest wall of the patient as during scanning, prior to performing ultrasound ablation.

15. A method in accordance with claim 9, wherein the needle is guided by a navigation system linked to the three-dimensional image including:
   a) a stereotactic frame secured to the breast with the needle attached to the stereotactic frame;
   b) a camera visually sensing an infrared marker on the needle; or
   c) a transmitter and receiver system coupled to the needle.

16. A method in accordance with claim 10, wherein ultrasound energy is directed using an ultrasound emitter guided by a navigation system linked to the three-dimensional image including:
   a) a stereotactic frame secured to the breast with the ultrasound emitter attached to the stereotactic frame;
   b) a camera visually sensing an infrared marker on the ultrasound emitter; or
   c) a transmitter and receiver system coupled to the ultrasound emitter.

17. A method in accordance with claim 10, further comprising:
   disposing the breast back into the bath and substantially maintaining the position and the shape of the breast with respect to the chest wall of the patient as during scanning, prior to directing ultrasound energy at the tumor.

18. A method in accordance with claim 11, wherein the probe is guided by a navigation system linked to the three-dimensional image including:
   a) a stereotactic frame secured to the breast with the probe attached to the stereotactic frame;
   b) a camera visually sensing an infrared marker on the probe; or
   c) a transmitter and receiver system coupled to the probe.

19. A method in accordance with claim 4, wherein the biopsy device, the marker placing device, the ultrasound emitter, the needle or the probe is guided by a navigation system linked to the three-dimensional image including:
   a) the biopsy device, the marker placing device, the ultrasound emitter, the needle or the probe being attached to a stereotactic frame;
   b) a camera visually sensing an infrared marker on the biopsy device, the marker placing device, the ultrasound emitter, the needle or the probe; or
   c) a transmitter and receiver system coupled to the biopsy device, the marker placing device, the ultrasound emitter, the needle or the probe.

20. A method for imaging and treating a breast of a patient, comprising:
   a) disposing the breast into a bath with a bath wall and containing a medium;
   b) physically securing the breast and maintaining the breast in a repeatable position and in a repeatable shape with respect to a chest wall of the patient by securing the breast to a frame suspended from a table supporting the patient;
   c) scanning the breast with ultrasound signals from transducer arrays to create a three-dimensional image of the breast and to locate a position of a tumor or a lesion in the breast with respect to the three-dimensional image;
   d) removing the breast from the bath by elevating the table with respect to the bath wall with the frame suspended from the table while maintaining the position and the shape of the breast with respect to the chest wall of the patient out of the bath as in the bath during scanning.

21. A method in accordance with claim 20, further comprising:
   positioning the patient on a table with the breast pendent through an aperture in the table; and
   maintaining the patient on the table with the breast pendent through the aperture while further treating the tumor or the lesion.

22. A method in accordance with claim 20, further comprising:
   performing a biopsy by inserting a biopsy device into the tumor or lesion and removing a tissue sample.

23. A method in accordance with claim 20, further comprising:
   inserting at least one marker into the breast to mark a margin of the tumor to guide a surgeon during surgery to remove the tumor.

24. A method in accordance with claim 20, further comprising performing surgery to remove the tumor using a surgical instrument including:
   a) a stereotactic frame secured to the breast with the surgical instrument attached to the stereotactic frame;
   b) a camera visually sensing an infrared marker on the surgical instrument; or
   c) a transmitter and receiver system coupled to the surgical instrument.

25. A method in accordance with claim 20, further comprising:
   performing ultrasound ablation by directing ultrasound energy at the tumor.

26. A method in accordance with claim 20, further comprising:
   injecting a chemotherapy drug into the tumor using a needle.

27. A method in accordance with claim 20, further comprising:
   injecting an ultrasound activated drug into the patient; and directing ultrasound energy at the tumor.

28. A method in accordance with claim 20, further comprising:
   thermally treating the tumor by inserting a probe with a hot tip or a cold tip into the tumor.

29. A method in accordance with claim 22, wherein the biopsy device is guided by a navigation system including:
   a) a stereotactic frame secured to the breast with the biopsy device attached to the stereotactic frame;
   b) a camera visually sensing an infrared marker on the biopsy device; or
   c) a transmitter and receiver system coupled to the biopsy device.

30. A method in accordance with claim 22, further comprising:

inserting at least one marker into the breast using the biopsy device to mark a margin of the tumor to guide a surgeon during surgery to remove the tumor.

31. A method in accordance with claim 25, further comprising:
disposing the breast back into the bath and substantially maintaining the position and the shape of the breast with respect to the chest wall of the patient as during scanning, prior to performing ultrasound ablation.

32. A method in accordance with claim 26, wherein the needle is guided by a navigation system linked to the three-dimensional coordinate system including:
 a) a stereotactic frame secured to the breast and the needle attached to the stereotactic frame;
 b) a camera visually sensing an infrared marker on the needle; or
 c) a transmitter and receiver system coupled to the needle.

33. A method in accordance with claim 27, wherein ultrasound energy is directed using an ultrasound emitter guided by a navigation system linked to the three-dimensional image including:
 a) a stereotactic frame secured to the breast and the ultrasound emitter attached to the frame;
 b) a camera visually sensing an infrared marker on the ultrasound emitter; or
 c) a transmitter and receiver system coupled to the ultrasound emitter.

34. A method in accordance with claim 27, further comprising:
disposing the breast back into the bath and substantially maintaining the position and the shape of the breast with respect to the chest wall of the patient as during scanning, prior to directing ultrasound energy at the tumor.

35. A method in accordance with claim 28, wherein the probe is guided by a navigation system linked to the three-dimensional image including:
 a) a stereotactic frame secured to the breast and the probe attached to the stereotactic frame;
 b) a camera visually sensing an infrared marker on the probe; or
 c) a transmitter and receiver system coupled to the probe.

36. A method for imaging and treating a breast of a patient, comprising:
 a) positioning the patient on a table with the breast pendent through an aperture in the table and into a bath with a bath wall and containing a medium;
 b) physically securing the breast and maintaining the breast in a repeatable position and in a repeatable shape with respect to a chest wall of the patient by securing the breast to a frame suspended from a table supporting the patient;
 c) scanning the breast with ultrasound signals from transducer arrays to create a three-dimensional image of the breast and to locate a position of a tumor or a lesion in the breast with respect to the three-dimensional image;
 d) removing the breast from the bath by elevating the table with respect to the bath with the frame suspended from the table;
 e) maintaining the position and the shape of the breast with respect to the chest wall of the patient out of the bath as in the bath during scanning; and
 f) further treating the tumor or the lesion of the breast with a treatment while maintaining the patient on the table and maintaining the position and the shape of the breast with respect to the chest wall of the patient, the treatment being selected from the group consisting of:
  i) performing a biopsy by inserting a biopsy device into the tumor or lesion and removing a tissue sample;
  ii) inserting at least one marker into the breast to mark a margin of the tumor with a marker placement device;
  iii) performing ultrasound ablation by directing ultrasound energy at the tumor with an ultrasound emitter;
  iv) injecting a drug into the tumor using a needle;
  v) injecting an ultrasound activated drug into the patient and directing ultrasound energy at the tumor with an ultrasound emitter;
  vi) thermally treating the tumor by inserting a probe with a hot tip or a cold tip into the tumor; or
  vii) performing surgery to remove the tumor using a surgical instrument.

37. A method in accordance with claim 36, wherein the biopsy device, the marker placing device, the ultrasound emitter, the needle, the probe or the surgical instrument is guided by a navigation system including:
 a) a stereotactic frame secured to the breast;
 b) a camera visually sensing an infrared marker on the biopsy device, the marker placing device, the ultrasound emitter, the needle, the probe or the surgical instrument; or
 c) a transmitter and receiver system coupled to the biopsy device, the marker placing device, the ultrasound emitter, the needle, the probe or the surgical instrument.

* * * * *